(12) United States Patent
Swayze et al.

(10) Patent No.: US 7,857,185 B2
(45) Date of Patent: Dec. 28, 2010

(54) DISPOSABLE LOADING UNIT FOR SURGICAL STAPLING APPARATUS

(75) Inventors: Jeffrey S. Swayze, Hamilton, OH (US); Thomas W. Huitema, Cincinnati, OH (US); Glen A. Armstrong, Hamilton, OH (US); Shailendra K. Parihar, Mason, OH (US); Donna L. Korvick, Maineville, OH (US); Richard W. Timm, Cincinnati, OH (US); Kevin R. Doll, Mason, OH (US); Bret W. Smith, King Mills, OH (US); William D. Kelly, Mason, OH (US); Ronald J. Kolata, Raleigh, NC (US); Joshua R. Uth, Mason, OH (US); Charles J. Scheib, Loveland, OH (US); Frederick E. Shelton, IV, Hillsboro, OH (US); William B. Weisenburgh, II, Maineville, OH (US); Jerome R. Morgan, Cincinnati, OH (US); Mark H. Ransick, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 286 days.

(21) Appl. No.: 12/031,539

(22) Filed: Feb. 14, 2008

(65) Prior Publication Data

US 2009/0206134 A1    Aug. 20, 2009

(51) Int. Cl.
*A61B 17/068* (2006.01)

(52) U.S. Cl. .................... 227/175.2; 227/19; 227/176.1

(58) Field of Classification Search .................. 227/19, 227/176.1, 175.1, 180.1, 175.2; 606/139, 606/219
See application file for complete search history.

(56) References Cited

U.S. PATENT DOCUMENTS

| | | | |
|---|---|---|---|
| 3,490,675 | A | 1/1970 | Green et al. |
| 3,643,851 | A | 2/1972 | Green et al. |
| 3,662,939 | A | 5/1972 | Bryan |

(Continued)

FOREIGN PATENT DOCUMENTS

CA    2458946 A1    3/2003

(Continued)

OTHER PUBLICATIONS

Disclosed Anonymously, "Motor-Driven Surgical Stapler improvements," Research Disclosure Database No. 526041, Published: Feb. 2008.

(Continued)

*Primary Examiner*—Scott A. Smith

(57) ABSTRACT

A disposable loading unit for operable attachment to a surgical stapling apparatus. The disposable loading unit may have a carrier that supports a staple cartridge and an anvil assembly that is movable coupled to the carrier. The various embodiments may further have an axial drive assembly that is configured to impart a closing motion to the anvil assembly and also supports a cutting blade thereon. The axial drive assembly is configured to receive firing motions and retraction motions from the surgical stapling apparatus. Various embodiments have an anvil release assembly that enables the anvil assembly to be released from a clamping orientation in the event that the cutting blade becomes jammed during operation.

23 Claims, 21 Drawing Sheets

U.S. PATENT DOCUMENTS

| | | |
|---|---|---|
| 3,717,294 A | 2/1973 | Green |
| 3,819,100 A | 6/1974 | Noiles et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,629,107 A | 12/1986 | Fedotov et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,869,414 A | 9/1989 | Green et al. |
| 4,869,415 A | 9/1989 | Fox |
| 4,941,623 A | 7/1990 | Pruitt |
| 4,944,443 A | 7/1990 | Oddsen et al. |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,211,649 A | 5/1993 | Kohler et al. |
| 5,221,036 A | 6/1993 | Takase |
| 5,222,975 A | 6/1993 | Crainich |
| 5,258,009 A | 11/1993 | Conners |
| 5,282,806 A | 2/1994 | Haber et al. |
| 5,282,829 A | 2/1994 | Hermes |
| 5,304,204 A | 4/1994 | Bregen |
| 5,342,395 A | 8/1994 | Jarrett et al. |
| 5,342,396 A | 8/1994 | Cook |
| 5,350,400 A | 9/1994 | Esposito et al. |
| 5,352,235 A | 10/1994 | Koros et al. |
| 5,366,479 A | 11/1994 | McGarry et al. |
| 5,383,895 A | 1/1995 | Holmes et al. |
| 5,397,324 A | 3/1995 | Carroll et al. |
| 5,413,272 A | 5/1995 | Green et al. |
| 5,417,361 A | 5/1995 | Williamson, IV |
| 5,425,745 A | 6/1995 | Green et al. |
| 5,474,566 A | 12/1995 | Alesi et al. |
| 5,478,354 A | 12/1995 | Tovey et al. |
| 5,480,089 A | 1/1996 | Blewett |
| 5,484,451 A | 1/1996 | Akopov et al. |
| 5,485,947 A | 1/1996 | Olson et al. |
| 5,487,499 A | 1/1996 | Sorrentino et al. |
| 5,489,058 A | 2/1996 | Plyley et al. |
| 5,497,933 A | 3/1996 | DeFonzo et al. |
| 5,503,320 A | 4/1996 | Webster et al. |
| 5,509,596 A | 4/1996 | Green et al. |
| 5,529,235 A | 6/1996 | Boiarski et al. |
| 5,535,934 A | 7/1996 | Boiarski et al. |
| 5,535,935 A | 7/1996 | Vidal et al. |
| 5,547,117 A | 8/1996 | Hamblin et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,580,067 A | 12/1996 | Hamblin et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,605,272 A | 2/1997 | Witt et al. |
| 5,605,273 A | 2/1997 | Hamblin et al. |
| 5,607,094 A | 3/1997 | Clark et al. |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,543 A | 12/1997 | Burdorff |
| 5,702,408 A | 12/1997 | Wales et al. |
| 5,704,534 A | 1/1998 | Huitema et al. |
| 5,706,997 A | 1/1998 | Green et al. |
| 5,711,472 A | 1/1998 | Bryan |
| 5,715,987 A | 2/1998 | Kelley et al. |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,255 A | 6/1998 | Chrisman et al. |
| 5,762,256 A | 6/1998 | Mastri et al. |
| 5,779,130 A | 7/1998 | Alesi et al. |
| 5,779,131 A | 7/1998 | Knodel et al. |

| | | |
|---|---|---|
| 5,779,132 A | 7/1998 | Knodel et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,820,009 A | 10/1998 | Melling et al. |
| 5,826,776 A | 10/1998 | Schulze et al. |
| 5,833,695 A | 11/1998 | Yoon |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,868,760 A | 2/1999 | McGuckin, Jr. |
| 5,878,937 A | 3/1999 | Green et al. |
| 5,894,979 A | 4/1999 | Powell |
| 5,897,562 A | 4/1999 | Bolanos et al. |
| 5,901,895 A | 5/1999 | Heaton et al. |
| 5,908,427 A | 6/1999 | McKean et al. |
| 5,911,353 A | 6/1999 | Bolanos et al. |
| 5,919,198 A | 7/1999 | Graves, Jr. et al. |
| 5,941,442 A | 8/1999 | Geiste et al. |
| 5,951,574 A | 9/1999 | Stefanchik et al. |
| 5,954,259 A | 9/1999 | Viola et al. |
| 6,010,054 A | 1/2000 | Johnson et al. |
| 6,032,849 A | 3/2000 | Mastri et al. |
| 6,045,560 A | 4/2000 | McKean et al. |
| 6,050,472 A | 4/2000 | Shibata |
| 6,079,606 A | 6/2000 | Milliman et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,109,500 A | 8/2000 | Alli et al. |
| 6,119,913 A | 9/2000 | Adams et al. |
| 6,126,058 A | 10/2000 | Adams et al. |
| 6,155,473 A | 12/2000 | Tompkins et al. |
| 6,168,605 B1 | 1/2001 | Measamer et al. |
| 6,171,330 B1 | 1/2001 | Benchetrit |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,330,965 B1 | 12/2001 | Milliman et al. |
| 6,387,113 B1 | 5/2002 | Hawkins et al. |
| 6,406,440 B1 | 6/2002 | Stefanchik |
| RE37,814 E | 8/2002 | Allgeyer |
| 6,436,107 B1 | 8/2002 | Wang et al. |
| 6,443,973 B1 | 9/2002 | Whitman |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,616,686 B2 | 9/2003 | Coleman et al. |
| 6,619,529 B2 | 9/2003 | Green et al. |
| 6,629,988 B2 | 10/2003 | Weadock |
| 6,644,532 B2 | 11/2003 | Green et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,233 B1 | 4/2004 | Whitman |
| 6,755,338 B2 | 6/2004 | Hahnen et al. |
| 6,769,594 B2 | 8/2004 | Orban, III |
| 6,773,438 B1 | 8/2004 | Knodel et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| RE38,708 E | 3/2005 | Bolanos et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,056,330 B2 | 6/2006 | Gayton |
| 7,059,508 B2 | 6/2006 | Shelton, IV et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,090,684 B2 | 8/2006 | McGuckin, Jr. et al. |
| 7,097,089 B2 | 8/2006 | Marczyk |
| 7,108,709 B2 | 9/2006 | Cummins |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,140,527 B2 | 11/2006 | Ehrenfels et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |

| Patent/Publication | Date | Inventor(s) |
|---|---|---|
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,730 B2 | 10/2008 | Viola |
| 7,434,715 B2 | 10/2008 | Shelton, IV et al. |
| 7,438,209 B1 | 10/2008 | Hess et al. |
| 7,441,685 B1 | 10/2008 | Boudreaux |
| 7,464,847 B2 | 12/2008 | Viola et al. |
| 7,472,814 B2 | 1/2009 | Mastri et al. |
| 7,481,347 B2 | 1/2009 | Roy |
| 7,490,749 B2 | 2/2009 | Schall et al. |
| 7,494,039 B2 | 2/2009 | Racenet et al. |
| 7,506,790 B2 | 3/2009 | Shelton, IV |
| 7,510,107 B2 | 3/2009 | Timm et al. |
| 7,546,940 B2 | 6/2009 | Milliman et al. |
| 7,549,564 B2 | 6/2009 | Boudreaux |
| 7,631,793 B2 | 12/2009 | Rethy et al. |
| 7,665,646 B2 | 2/2010 | Prommersberger |
| 2002/0117534 A1 | 8/2002 | Green et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0254608 A1 | 12/2004 | Huitema et al. |
| 2005/0059997 A1 | 3/2005 | Bauman et al. |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0100643 A1 | 5/2006 | Laufer et al. |
| 2006/0180634 A1 | 8/2006 | Shelton, IV et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0045379 A1 | 3/2007 | Shelton, IV |
| 2007/0073340 A1 | 3/2007 | Shelton, IV et al. |
| 2007/0073341 A1 | 3/2007 | Smith |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0246505 A1 | 10/2007 | Pace-Floridia et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |

| | | |
|---|---|---|
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308606 A1 | 12/2008 | Timm et al. |
| 2008/0308607 A1 | 12/2008 | Timm et al. |
| 2008/0308608 A1 | 12/2008 | Prommersberger |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0090763 A1 | 4/2009 | Zemlok et al. |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255978 A1 | 10/2009 | Viola et al. |
| 2009/0289096 A1 | 11/2009 | Shelton, IV et al. |
| 2010/0032470 A1 | 2/2010 | Hess et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0213241 A1 | 8/2010 | Bedi et al. |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 1775926 A | 1/1972 |
| DE | 9412228 U | 9/1994 |
| DE | 19924311 A1 | 11/2000 |
| DE | 69328576 T2 | 1/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0070230 B1 | 10/1985 |
| EP | 0033548 B1 | 5/1986 |
| EP | 0276104 A2 | 7/1988 |
| EP | 0639349 A2 | 2/1994 |
| EP | 0324636 B1 | 3/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |
| EP | 0770355 A1 | 5/1997 |
| EP | 0503662 B1 | 6/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0676173 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0741996 B1 | 2/2004 |
| EP | 0705570 B1 | 4/2004 |
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |

| | | | | | | |
|---|---|---|---|---|---|---|
| EP | 1479348 | A1 | 11/2004 | WO | WO 95/18572 A1 | 7/1995 |
| EP | 1520521 | A1 | 4/2005 | WO | WO 95/23557 A1 | 9/1995 |
| EP | 1520523 | A1 | 4/2005 | WO | WO 95/29639 A1 | 11/1995 |
| EP | 1520525 | A1 | 4/2005 | WO | WO 96/22055 A1 | 7/1996 |
| EP | 1522264 | A1 | 4/2005 | WO | WO 96/35464 A1 | 11/1996 |
| EP | 1550408 | A1 | 7/2005 | WO | WO 97/34533 A1 | 9/1997 |
| EP | 1557129 | A1 | 7/2005 | WO | WO 97/39688 A2 | 10/1997 |
| EP | 1064883 | B1 | 8/2005 | WO | WO 98/17180 A1 | 4/1998 |
| EP | 1157666 | B1 | 9/2005 | WO | WO 98/30153 A1 | 7/1998 |
| EP | 1621138 | A2 | 2/2006 | WO | WO 99/12483 A1 | 3/1999 |
| EP | 1621139 | A2 | 2/2006 | WO | WO 99/15086 A1 | 4/1999 |
| EP | 1621141 | A2 | 2/2006 | WO | WO 99/34744 A1 | 7/1999 |
| EP | 1621145 | A2 | 2/2006 | WO | WO 99/45849 A1 | 9/1999 |
| EP | 1621151 | A2 | 2/2006 | WO | WO 00/24322 A1 | 5/2000 |
| EP | 1652481 | A2 | 5/2006 | WO | WO 00/057796 A1 | 10/2000 |
| EP | 1382303 | B1 | 6/2006 | WO | WO 00/64365 A1 | 11/2000 |
| EP | 1045672 | B1 | 8/2006 | WO | WO 00/72762 A1 | 12/2000 |
| EP | 1617768 | B1 | 8/2006 | WO | WO 00/72765 A1 | 12/2000 |
| EP | 1702567 | A2 | 9/2006 | WO | WO 01/05702 A1 | 1/2001 |
| EP | 1129665 | B1 | 11/2006 | WO | WO 01/10482 A1 | 2/2001 |
| EP | 1256317 | B1 | 12/2006 | WO | WO 01/54594 A1 | 8/2001 |
| EP | 1728473 | A1 | 12/2006 | WO | WO 01/62158 A2 | 8/2001 |
| EP | 1728475 | A2 | 12/2006 | WO | WO 01/62162 A1 | 8/2001 |
| EP | 1479346 | B1 | 1/2007 | WO | WO 01/62164 A2 | 8/2001 |
| EP | 1484024 | B1 | 1/2007 | WO | WO 01/91646 A1 | 12/2001 |
| EP | 1754445 | A2 | 2/2007 | WO | WO 02/07608 A2 | 1/2002 |
| EP | 1759812 | A1 | 3/2007 | WO | WO 02/07618 A1 | 1/2002 |
| EP | 1769756 | A1 | 4/2007 | WO | WO 02/17799 A1 | 3/2002 |
| EP | 1769758 | A1 | 4/2007 | WO | WO 02/19920 A1 | 3/2002 |
| EP | 1785097 | A2 | 5/2007 | WO | WO 02/30297 A2 | 4/2002 |
| EP | 1790293 | A2 | 5/2007 | WO | WO 02/32322 A2 | 4/2002 |
| EP | 1800610 | A1 | 6/2007 | WO | WO 02/43571 A2 | 6/2002 |
| EP | 1300117 | B1 | 8/2007 | WO | WO 02/058568 A1 | 8/2002 |
| EP | 1813199 | A1 | 8/2007 | WO | WO 02/060328 A1 | 8/2002 |
| EP | 1813201 | A1 | 8/2007 | WO | WO 02/067785 A2 | 9/2002 |
| EP | 1813203 | A2 | 8/2007 | WO | WO 02/098302 A1 | 12/2002 |
| EP | 1813207 | A1 | 8/2007 | WO | WO 03/000138 A2 | 1/2003 |
| EP | 1813209 | A1 | 8/2007 | WO | WO 03/001329 A2 | 1/2003 |
| EP | 1839596 | A1 | 10/2007 | WO | WO 03/013363 A1 | 2/2003 |
| EP | 1402821 | B1 | 12/2007 | WO | WO 03/020106 A2 | 3/2003 |
| EP | 1872727 | A1 | 1/2008 | WO | WO 03/020139 A2 | 3/2003 |
| EP | 1897502 | A1 | 3/2008 | WO | WO 03/079909 A3 | 3/2003 |
| EP | 1702568 | B1 | 7/2008 | WO | WO 03/030743 A2 | 4/2003 |
| EP | 1970014 | A1 | 9/2008 | WO | WO 03/037193 A1 | 5/2003 |
| EP | 1980213 | A2 | 10/2008 | WO | WO 03/047436 A3 | 6/2003 |
| EP | 1759645 | B1 | 11/2008 | WO | WO 03/057048 A1 | 7/2003 |
| EP | 1693008 | B1 | 12/2008 | WO | WO 03/057058 A1 | 7/2003 |
| EP | 2000102 | A2 | 12/2008 | WO | WO 03/063694 A1 | 8/2003 |
| EP | 1749486 | B1 | 3/2009 | WO | WO 03/077769 A1 | 9/2003 |
| EP | 2090256 | A2 | 8/2009 | WO | WO 03/082126 A1 | 10/2003 |
| EP | 1813206 | B1 | 4/2010 | WO | WO 03/088845 A2 | 10/2003 |
| FR | 999646 | A | 2/1952 | WO | WO 03/090630 A2 | 11/2003 |
| FR | 1112936 | A | 3/1956 | WO | WO 03/094743 A1 | 11/2003 |
| FR | 2765794 | A | 1/1999 | WO | WO 03/094745 A1 | 11/2003 |
| GB | 939929 | A | 10/1963 | WO | WO 03/094746 A1 | 11/2003 |
| GB | 1210522 | A | 10/1970 | WO | WO 03/094747 A1 | 11/2003 |
| GB | 2336214 | A | 10/1999 | WO | WO 03/101313 A1 | 12/2003 |
| JP | 6007357 | A | 1/1994 | WO | WO 03/105698 A2 | 12/2003 |
| JP | 7051273 | A | 2/1995 | WO | WO 03/105702 A2 | 12/2003 |
| JP | 8033641 | A | 2/1996 | WO | WO 2004/006980 A1 | 1/2004 |
| JP | 8229050 | A | 9/1996 | WO | WO 2004/028585 A2 | 4/2004 |
| JP | 2000287987 | A | 10/2000 | WO | WO 2004/032754 A2 | 4/2004 |
| JP | 2001286477 | A | 10/2001 | WO | WO 2004/032760 A2 | 4/2004 |
| JP | 2002369820 | A | 12/2002 | WO | WO 2004/032762 A1 | 4/2004 |
| JP | 2005505322 | T | 2/2005 | WO | WO 2004/032763 A2 | 4/2004 |
| JP | 2005103293 | A | 4/2005 | WO | WO 2004/047653 A2 | 6/2004 |
| RU | 2187249 | C2 | 8/2002 | WO | WO 2004/049956 A2 | 6/2004 |
| RU | 2225170 | C2 | 3/2004 | WO | WO 2004/086987 A1 | 10/2004 |
| SU | 1377053 | A1 | 2/1988 | WO | WO 2004/096057 A2 | 11/2004 |
| SU | 1561964 | A1 | 5/1990 | WO | WO 2004/105621 A2 | 12/2004 |
| SU | 1722476 | A1 | 3/1992 | WO | WO 2004/112618 A2 | 12/2004 |
| WO | WO 93/08755 | A1 | 5/1993 | WO | WO 2004/112652 A2 | 12/2004 |

| | | | |
|---|---|---|---|
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

European Search Report, Application No. 09250385.3, dated May 14, 2009 (6 pages).

U.S. Appl. No. 11/820,077, filed Jun. 18, 2007.

European Search Opinion, Application No. 09250385.3, dated Mar. 1, 2010 (4 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

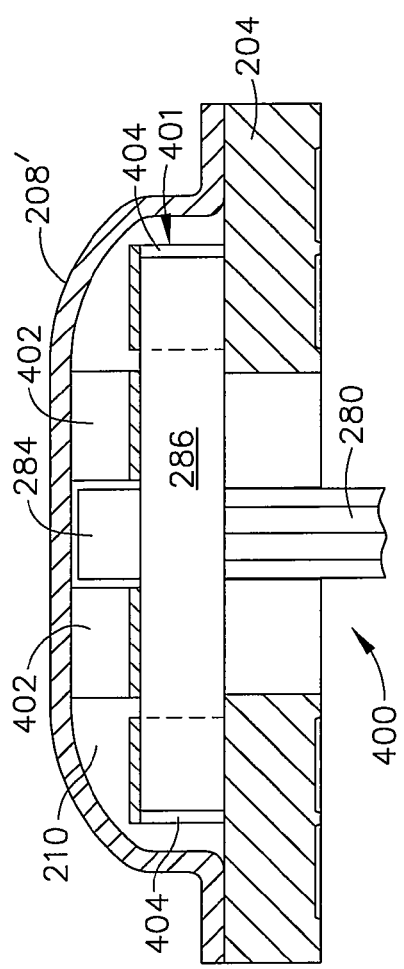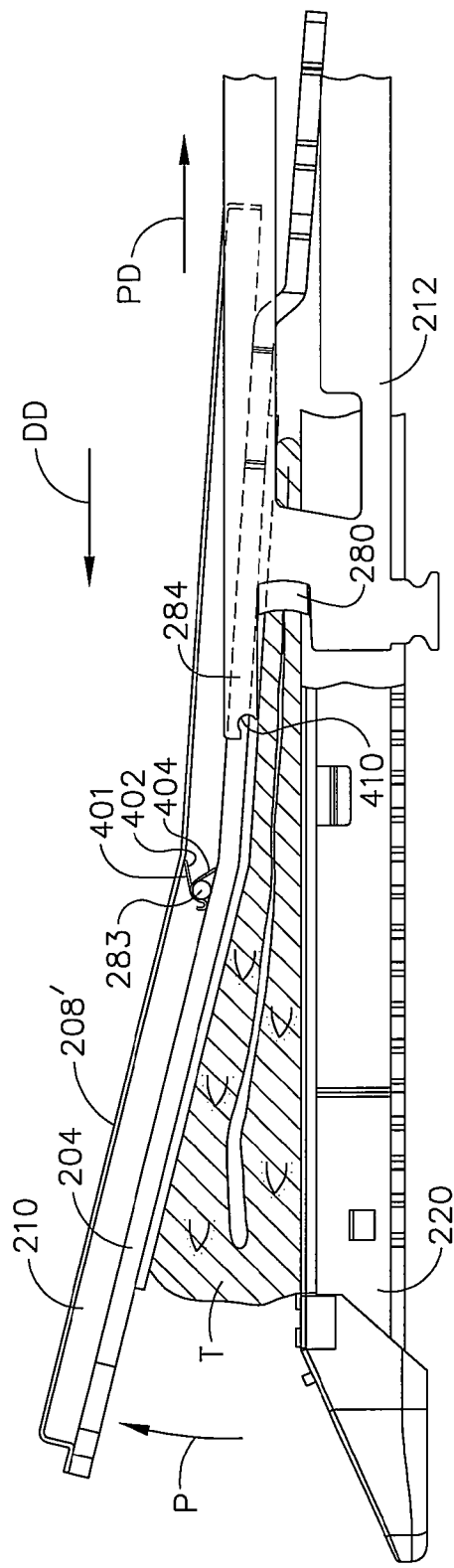

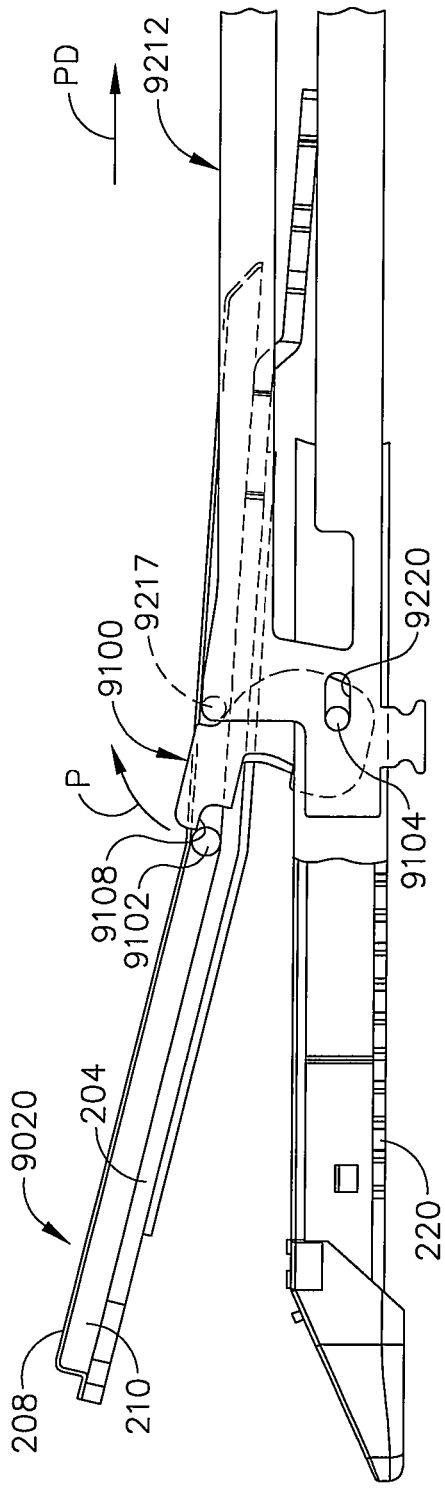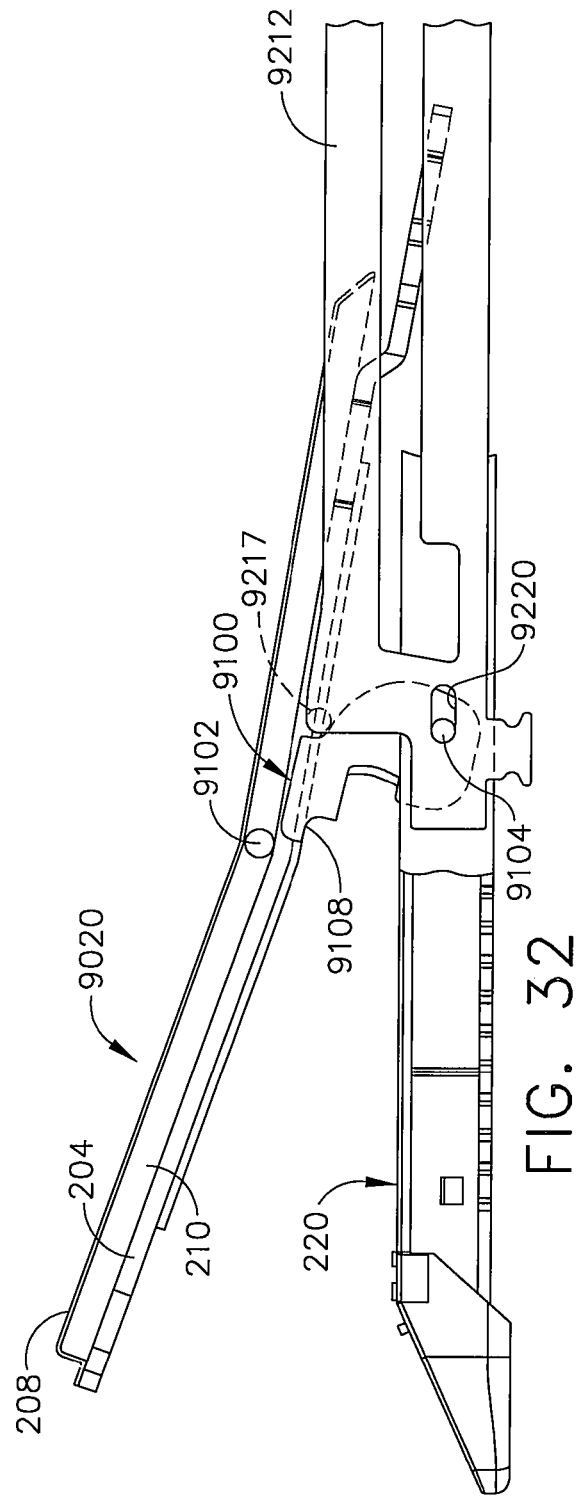

DISPOSABLE LOADING UNIT FOR SURGICAL STAPLING APPARATUS

FIELD OF THE INVENTION

The present invention relates in general to endoscopic surgical instruments including, but not limited to, surgical stapler instruments that have disposable loading units that are capable of applying lines of staples to tissue while cutting the tissue between those staple lines and, more particularly, to improvements relating to such disposable loading units.

BACKGROUND

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members supports a staple cartridge that has at least two laterally spaced rows of staples. The other jaw member defines an anvil having staple-forming pockets aligned with the rows of staples in the cartridge. The instrument commonly includes a plurality of reciprocating wedges which, when driven distally, pass through openings in the staple cartridge and engage drivers supporting the staples to effect the firing of the staples toward the anvil.

Different types of surgical staplers suitable for endoscopic applications are known. For example, on type of surgical stapling instrument is configured to operate with disposable loading units (DLU's) that are constructed to support a staple cartridge and knife assembly therein. Once the procedure is completed, the entire DLU is discarded. Such instruments that are designed to accommodate DLU's purport to offer the advantage of a "fresh" knife blade for each firing of the instrument. Examples of such surgical stapling apparatuses and DLU's are disclosed in U.S. Pat. No. 5,865,361 to Milliman et al., the disclosure of which is herein incorporated by reference in its entirety.

Prior surgical stapling apparatuses, such as those disclosed in U.S. Pat. No. 5,865,361, suffer from the inability to be fired in thicker tissues (e.g., tissues with thicknesses greater than 3.5 mm) due to the increased loads applied to their firing systems. Such increased loads can, for example, increase the likelihood that the firing system will fail when the blade is still in the anvil and may therefore require that the tool assembly thereof be cut off of the tissue which may lead to serious injury consequences for the patient.

Thus, there is a need for a disposable loading unit that can be easily opened in the event that the blade becomes jammed as it is driven through the tissue that is clamped in the unit.

SUMMARY

In one general aspect of various embodiments of the present invention there is provided a disposable loading unit for attachment to a surgical stapling apparatus. The disposable loading unit may comprise a staple cartridge that is supported in a carrier that is operably couplable to the surgical stapling apparatus. An anvil assembly may be movably coupled to the carrier for selective movable travel between open and closed positions relative to the staple cartridge. The disposable loading unit may further comprise an axial drive assembly that has a distal end portion that is constructed to move in a distal direction through a slot in the staple cartridge in response to a drive motion imparted to the axial drive assembly from the surgical stapling apparatus and also move in a proximal direction through the slot in the staple cartridge in response to a retraction motion applied to the axial drive assembly from the surgical stapling apparatus. The distal end portion of the axial drive assembly may be configured to impart a closing force to the anvil assembly as the axial drive assembly is driven in the distal direction in the slot in the staple cartridge. The disposable loading unit may further include an anvil release assembly that operably cooperates with the distal end portion of the axial drive assembly and the anvil assembly for selectively causing the distal end portion of the axial drive assembly to discontinue imparting the closing force to the anvil assembly regardless of where the distal end portion of the axial drive assembly is located within the slot in the staple cartridge.

In still another general aspect of various embodiments of the present invention there is provided a disposable loading unit for attachment to a surgical stapling apparatus. In various embodiments, the disposable loading unit includes a staple cartridge that is supported in a carrier that is operably couplable to the surgical stapling apparatus. An anvil portion is pivotally coupled to the carrier for selective pivotable travel between open and closed positions relative to the staple cartridge. The anvil portion has an axial anvil slot therethrough. An anvil cover may be attached to the anvil portion to define an anvil cavity therebetween. The disposable loading unit may further include an axial drive assembly that has a distal end portion that is constructed to move in a distal direction through a cartridge slot in the staple cartridge as well as the anvil slot in response to a drive motion imparted to the axial drive assembly from the surgical stapling apparatus and also move in a proximal direction through the cartridge slot and the anvil slot in response to a retraction motion applied to the axial drive assembly from the surgical stapling apparatus. A transverse anvil pin may be detachably supported on a retention flange portion of the axial drive assembly such that the anvil pin is movably received in the anvil cavity and spans the anvil slot. A disengagement member may be provided on the transverse anvil pin and is oriented to engage at least a portion of at least one of the anvil cover and the anvil portion when a retraction motion is applied to the axial drive assembly regardless of where the distal end portion of the axial drive assembly is located within the cartridge slot to thereby cause the anvil pin to be decoupled from the axial drive assembly.

In another general aspect of various embodiments of the present invention there is provided a surgical stapling apparatus. In various embodiments, the surgical stapling apparatus comprises a handle assembly that has an elongated body operably coupled thereto. A disposable loading unit is operably coupled to the elongated body. Various embodiments of the disposable loading unit may comprise a carrier that is operably couplable to a distal end of the elongated body. A staple cartridge may be supported in the carrier. An anvil assembly may be movably coupled to the carrier for selective movable travel between open and closed positions relative to the staple cartridge. The disposable loading unit may further comprise an axial drive assembly that has a distal end portion that is constructed to move in a distal direction through a slot in the staple cartridge in response to a drive motion imparted to the axial drive assembly from the handle assembly and also move in a proximal direction through the slot in the staple cartridge in response to a retraction motion applied to the axial drive assembly from the handle assembly. The distal end portion of the axial drive assembly may be configured to impart a closing force to the anvil assembly as the axial drive assembly is driven in the distal direction in the slot in the staple cartridge. A pair of support bars may be movably supported within an axial slot in the anvil assembly. The support bars may be spaced from each other to permit the distal end portion of the axial drive assembly to movably pass therebetween. The support bars may be selectively movable between the first position wherein the support bars support an anvil pin attached to the distal end portion of the axial drive assembly and retracted positions wherein the anvil pin is not supported by the support bars and is permitted to disengage the anvil assembly. A connector link may be coupled to the support bars and a retraction link may be operably supported in the elongated body and configured to operably engage the connector link. An actuator knob may be operably supported on the elongated body such that it can interact with the retraction link to enable retraction motions to be applied to the retraction link and the connector link upon actuation of the actuator knob.

BRIEF DESCRIPTION OF THE FIGURES

The accompanying drawings, which are incorporated in and constitute a part of this specification, illustrate embodiments of the invention, and, together with the general description of various embodiments of the invention given above, and the detailed description of the embodiments given below, serve to explain various principles of the present invention.

FIG. 10 is a cross-sectional view of the anvil assembly depicted in FIG. 9, taken along line 10-10 in FIG. 9.

FIG. 11 is a partial side view of a portion of a disposable loading unit embodiment of the present invention clamping tissue between the anvil assembly and the staple cartridge.

FIG. 31 is another side view of the disposable loading unit of FIGS. 29 and 30 wherein the axial drive assembly has been retracted to start the release of the anvil pin from the anvil arm.

FIG. 32 is another side view of the disposable loading unit of FIGS. 29-31 wherein the anvil pin has been completely disengaged from the anvil arm.

DETAILED DESCRIPTION

Figure 1:
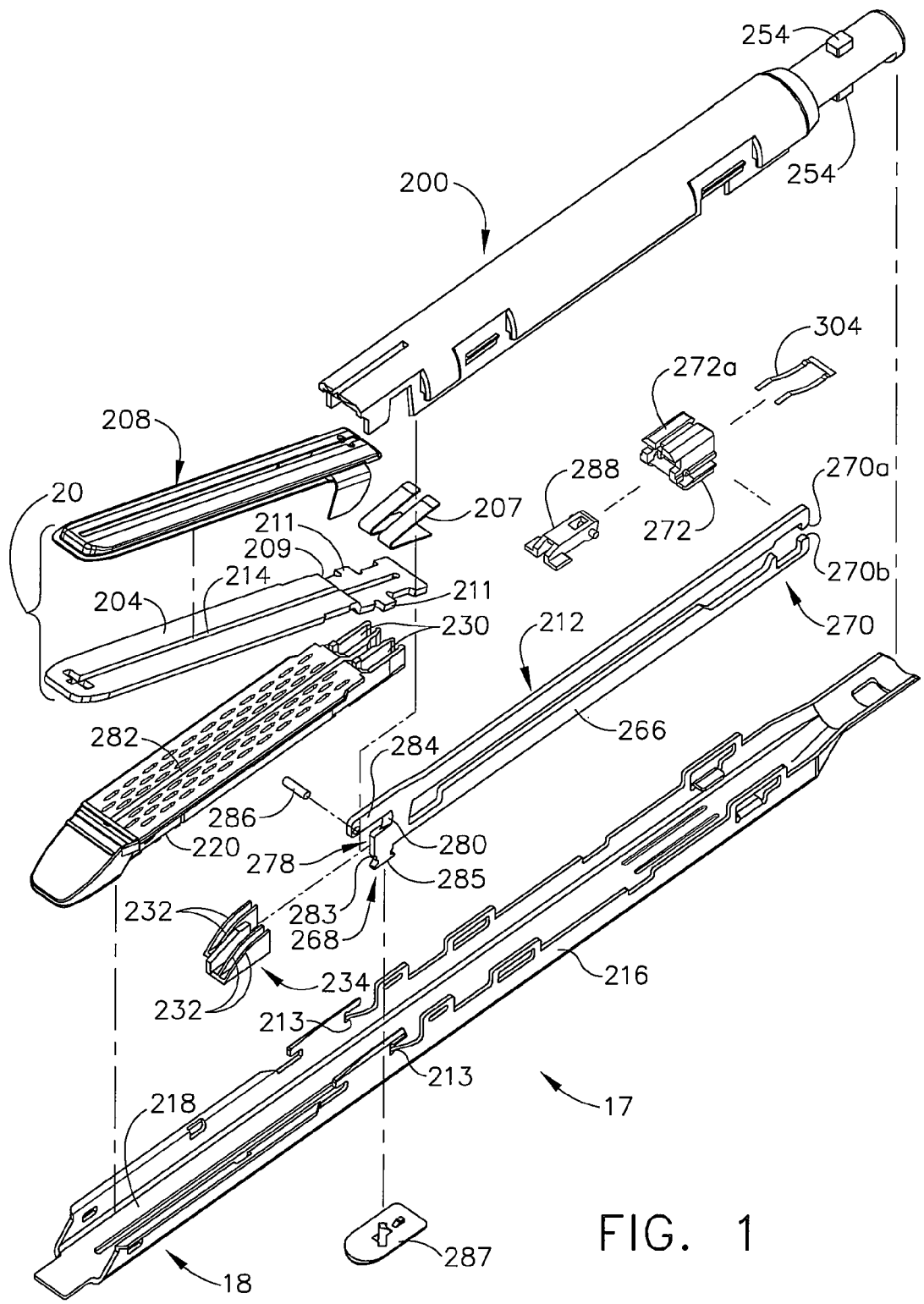
FIG. 1 is an exploded assembly view of a non-articulatable disposable loading unit.

Turning to the Drawings, wherein like numerals denote like components throughout the several views, FIG. 1 depicts a non-articulatable disposable loading unit 16 that may be used in connection with a surgical stapling apparatus in a manner discussed in U.S. Pat. No. 5,865,361, the disclosure of which is herein incorporated by reference. It will be appreciated that the terms "proximal" and "distal" are used herein with reference to a clinician gripping the handle assembly of the surgical stapling apparatus. Thus, the disposable loading unit 16 is distal with respect to the more proximal handle assembly. It will be further appreciated that, for convenience and clarity, spatial terms such as "vertical", "horizontal", "up", "down", "right", and "left" are used herein with respect to the drawings. However, surgical instruments are used in many orientations and positions, and these terms are not intended to be limiting and absolute.

As can be seen in FIG. 1, a non-articulatable disposable loading unit 16 may generally comprise a tool assembly 17 for performing surgical procedures such as cutting tissue and applying staples on each side of the cut. In particular, the tool assembly includes a cartridge assembly 18 that houses a plurality of surgical staples therein. The tool assembly 17 also includes a staple-forming anvil assembly 20 that has an anvil portion 204 that has a plurality of staple deforming concavities (not shown) formed in the undersurface thereof. A cover plate 208 is commonly secured to a top surface of anvil portion 204 to define an anvil cavity therebetween. The anvil cavity is dimensioned to receive a distal end of an axial drive assembly 212. A longitudinal slot 214 extends through anvil portion 204 to facilitate passage of retention flange 284 of axial drive assembly 212 into the anvil cavity. A camming surface 209 is formed on a proximal end of anvil portion 204 and is positioned to engage axial drive assembly 212 to facilitate closing of the anvil assembly 20.

Cartridge assembly 18 generally includes a carrier 216 which defines an elongated support channel 218. Elongated support channel 218 is dimensioned and configured to receive a staple cartridge 220 therein. Such staple cartridge 220 supports a plurality of fasteners and pushers as is known in the art. A plurality of spaced-apart longitudinal slots 230 extend through staple cartridge 220 to accommodate upstanding cam wedges 232 of an actuation sled 234. A central longitudinal slot 282 extends along the length of staple cartridge 220 to facilitate passage of a knife blade 280 formed on the axial drive assembly 212. During operation of the disposable loading unit 16, actuation sled 234 translates through longitudinal slots 230 of staple cartridge 220 to advance cam wedges 232 into sequential contact with the pushers that are operably supported in the cartridge 220 to cause the pushers to translate vertically within the cartridge 220 and urge the fasteners (staples) associated with the pushers into the staple deforming cavities of the anvil assembly 20. A pair of pivot members 211 are formed on the proximal end of the anvil portion 204 and are configured to be received in slots 213 that are formed in carrier 216 to enable the anvil portion 204 to pivot between the open and tissue-clamping positions.

As can also be seen in FIG. 1, the disposable loading unit 16 also has a housing portion 200 that is adapted to snap onto or otherwise be attached to the carrier 216. The axial drive assembly 212 includes an elongated drive beam 266 that has a distal working head 268 and a proximal engagement section 270. As is known, the drive beam 266 may be constructed from a single sheet of material or, preferably, from multiple stacked sheets. Engagement section 270 includes a pair of engagement fingers 270a and 270b that are dimensioned and configured to mountingly engage a pair of corresponding retention slots 272a formed in a drive member 272. Drive member 272 may include a proximal porthole (not shown) that is configured to receive the distal end of a control rod as discussed in U.S. Pat. No. 5,865,361.

The distal end of drive beam 266 includes a vertical support strut 278 which supports the knife blade 280, and an abutment surface 283 which engages the central portion of actuation sled 234 during a stapling procedure. Surface 285 is located at the base of surface 283 and is configured to receive a support member 287 that is slidably positioned along the bottom of the carrier 216. Knife blade 280 is generally positioned to translate slightly behind actuation sled 234 through a central longitudinal slot 282 in staple cartridge 220 to form an incision between rows of stapled body tissue.

A retention flange 284 projects distally from vertical strut 278 and supports a camming pin 286 at its distal end. Camming pin 286 is dimensioned and configured to engage camming surface 209 on anvil portion 204 to clamp anvil portion 204 against body tissue. In addition, a leaf spring 207 may be provided between the proximal end of the anvil portion 204 and the distal end portion of the housing 200 to bias the anvil assembly 20 to a normally open position. The disposable loading unit 16 may further include a lockout device 288 and spring 304 arrangement as described in U.S. Pat. No. 5,865,361.

Figure 2:
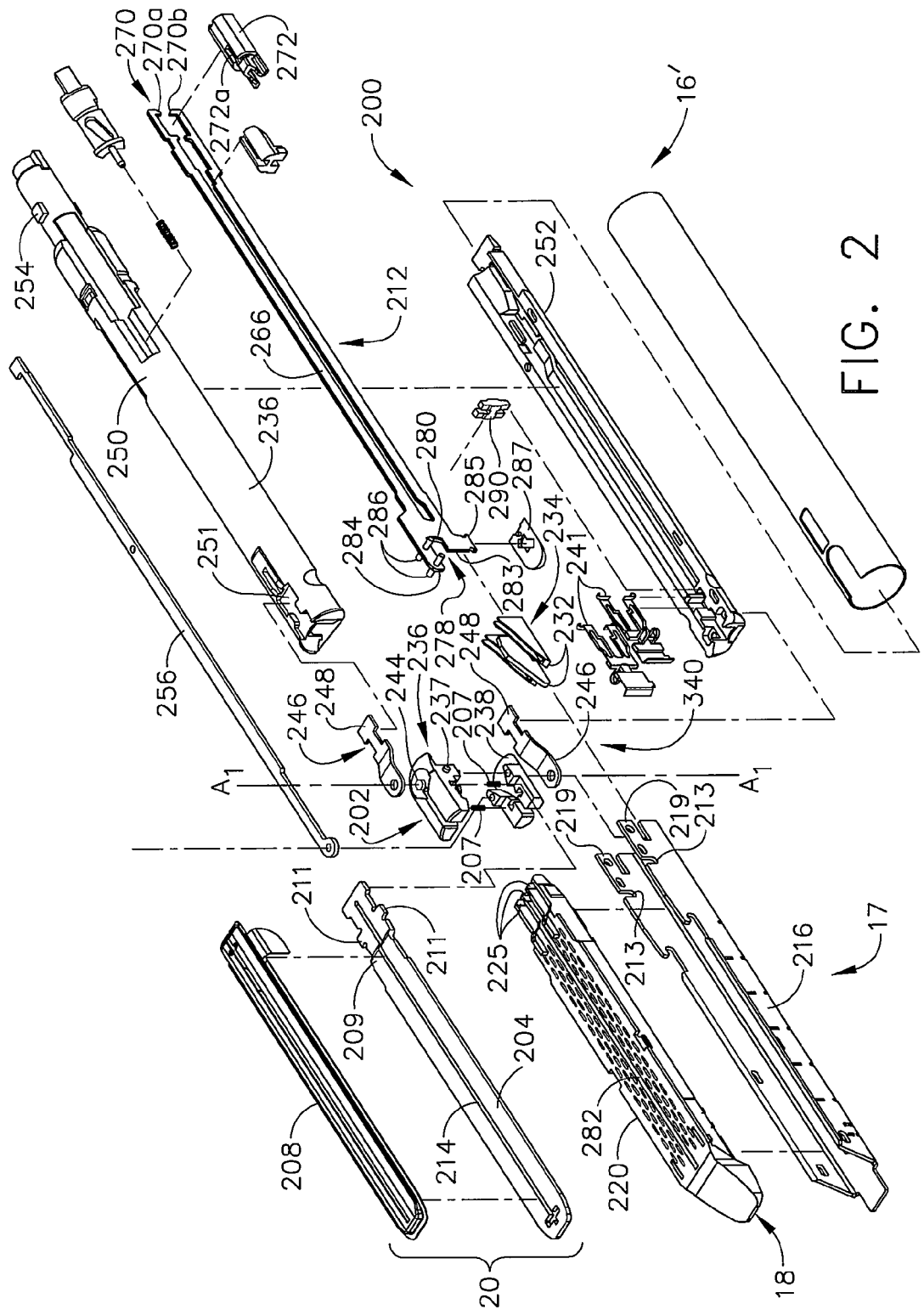
FIG. 2 is an exploded assembly view of an articulatable disposable loading unit.

FIG. 2 illustrates an articulatable disposable loading unit 16' that includes a tool assembly 17 that has an anvil assembly 20 and cartridge assembly 18. Anvil assembly 20 includes and anvil portion 204 that has a plurality of staple deforming concavities (not shown) formed in the undersurface thereof. A cover plate 208 is secured to a top surface of anvil portion 204 to define an anvil cavity therebetween. The anvil cavity is dimensioned to receive a distal end of an axial drive assembly 212. A longitudinal slot 214 extends through anvil portion 204 to facilitate passage of retention flange 284 of axial drive assembly 212 into the anvil cavity. A camming surface 209 formed on anvil portion 204 may be positioned to engage axial drive assembly 212 to facilitate clamping of tissue between the anvil assembly 20 and the cartridge 18.

The cartridge assembly 18 includes a carrier 216 that supports a staple cartridge 220 therein. Staple cartridge 220 includes retention slots 225 for receiving a plurality of fasteners (staples) and pushers. A plurality of spaced apart longitudinal slots 230 extend through staple cartridge 220 to accommodate upstanding cam wedges 232 of an actuation sled 234. A central longitudinal slot 282 extends along the length of staple cartridge 220 to facilitate passage of a knife blade 280. During operation of the disposable loading unit 16', actuation sled 234 translates through longitudinal slots 230 of staple cartridge 220 to advance cam wedges 232 into sequential contact with the pushers that are operably supported in the cartridge 220 to cause the pushers to urge the fasteners into the staple deforming cavities of the anvil assembly 20. A pair of pivot members 211 are formed on anvil portion 204 and are positioned within slots 213 formed in the carrier 216 to guide the anvil portion 204 between the open and tissue-clamping positions.

The articulatable loading unit 16' further includes a housing portion 200 that comprises an upper housing half 250 and a lower housing half 252. The proximal end of housing half 250 may include engagement nubs 254 for releasably engaging elongated body 14. Nubs 254 form a bayonet type coupling with the distal end of body 14 as described in U.S. Pat. No. 5,865,361. As can also be seen in FIG. 2, the axial drive assembly 212 includes an elongated drive beam 266 that has a distal working head 268 and a proximal engagement section 270. Drive beam 266 may be constructed from a single sheet of material or, preferably, from multiple stacked sheets. Engagement section 270 includes a pair of engagement fingers 270a and 270b that are dimensioned and configured to mountingly engage a pair of corresponding retention slots 272a formed in a drive member 272. Drive member 272 includes a proximal porthole (not shown) configured to receive the distal end of control rod 52 when the proximal end of disposable loading unit 16' is engaged with elongated body 14 of a surgical stapling apparatus as disclosed in U.S. Pat. No. 5,865,361. The distal end of drive beam 266 is defined by a vertical support strut 278 which supports a knife blade 280, and an abutment surface 283 which engages the central portion of actuation sled 234 during a stapling procedure. Surface 285 at the base of surface 283 may be configured to receive a support member 287 that is slidably positioned along the bottom of the carrier 216. Knife blade 280 is generally positioned to translate slightly behind actuation sled 234 through a central longitudinal slot 282 in staple cartridge 220 to form an incision between rows of stapled body tissue. To provide support to the drive beam 266 within the housing 200 as the drive beam 266 is advanced axially, a blade stabilizing member 290 is mounted within the housing 200. A retention flange 284 projects distally from vertical strut 278 and supports a pair of cylindrical cam rollers 286 at its distal end. Cam rollers 286 are dimensioned and configured to engage camming surface 209 on anvil portion 204 to clamp anvil portion 204 against body tissue.

Figure 3:
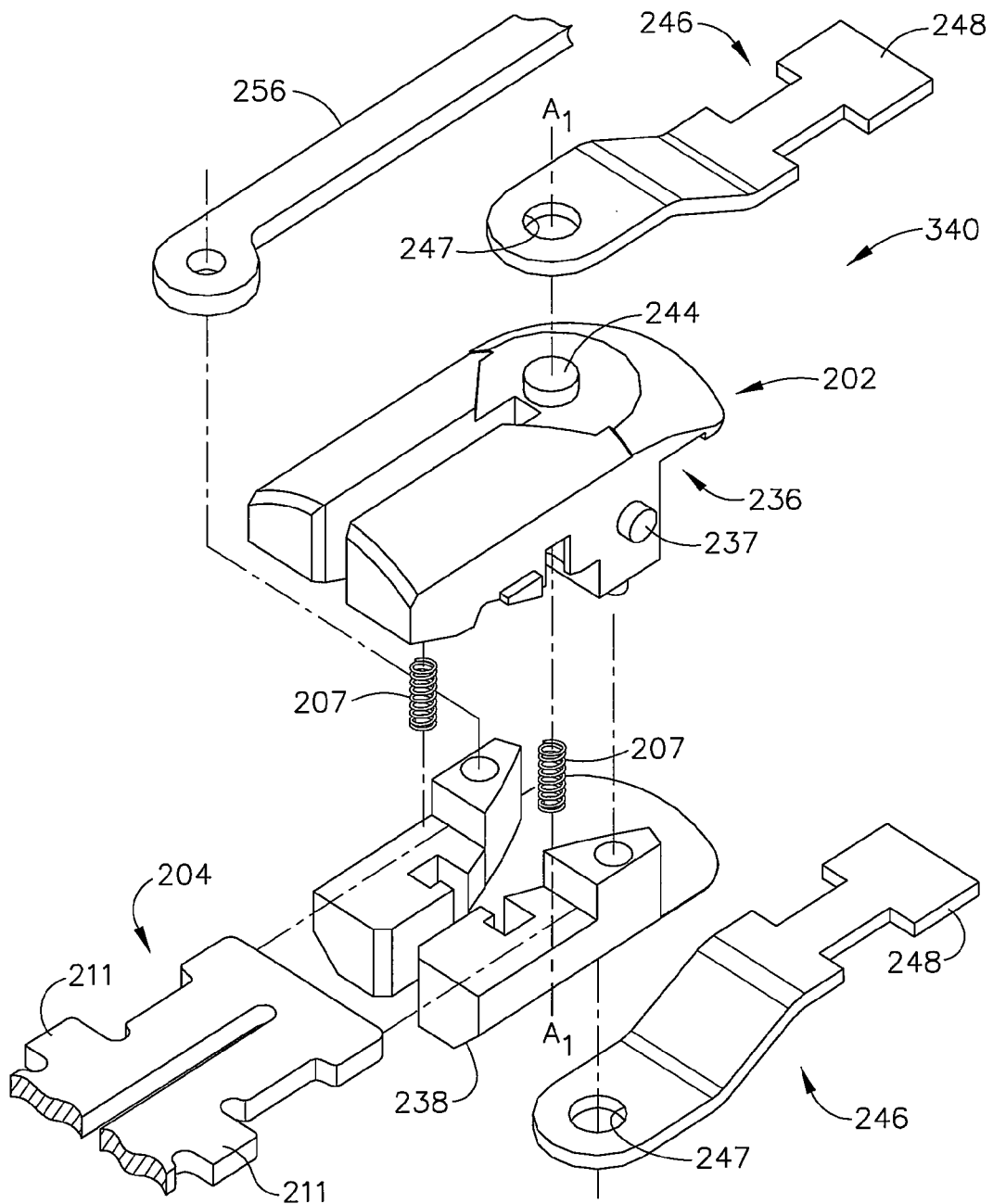
FIG. 3 is a partial exploded assembly view of the articulation joint of a prior articulatable disposable loading unit of FIG. 2.

As can be seen in FIGS. 2 and 3, the articulatable reload unit 16' includes an articulation joint 340 that includes a mounting assembly 202 that comprises an upper mounting portion 236 and a lower mounting portion 238. A pivot pin 244 is formed on each of the mounting portions 236, 238 and serve to define a pivot axis "A1-A1" which may be substantially perpendicular to the longitudinal axis "L-L" of the articulatable disposable loading unit 16'. The mounting assembly 202 is pivotally coupled to the distal end of the housing assembly 200 by a pair of coupling members 246. Coupling members 246 each have a hole 247 therethrough for receiving a corresponding pin 244 therethrough. The proximal end 248 of each coupling member 246 is configured to be interlockingly received in a corresponding groove 251 formed in the distal end of the upper housing half 250 and the distal end of the lower housing half 252. A pair of springs 207 are provided between the proximal end of the anvil portion 204 and the upper mounting portion 236 to bias the anvil assembly 20 to a normally open position. An articulation link 256 may be provided to articulate the tool assembly 17 about the articulation axis "A1-A1" relative to the housing assembly 200 as is taught in U.S. Pat. No. 5,865,361.

Prior disposable loading units may suffer from the inability to be fired in thicker tissues (e.g., tissues with thicknesses greater than 3.5 mm) due to the increased loads applied to the firing system. Such increased loads can, for example, increase the likelihood that the firing system will fail when the blade 280 is still in the anvil assembly 20 and may therefore require that the tool assembly 17 be cut off of the tissue. Such failure mode can have serious patient injury consequences.

Figure 4:
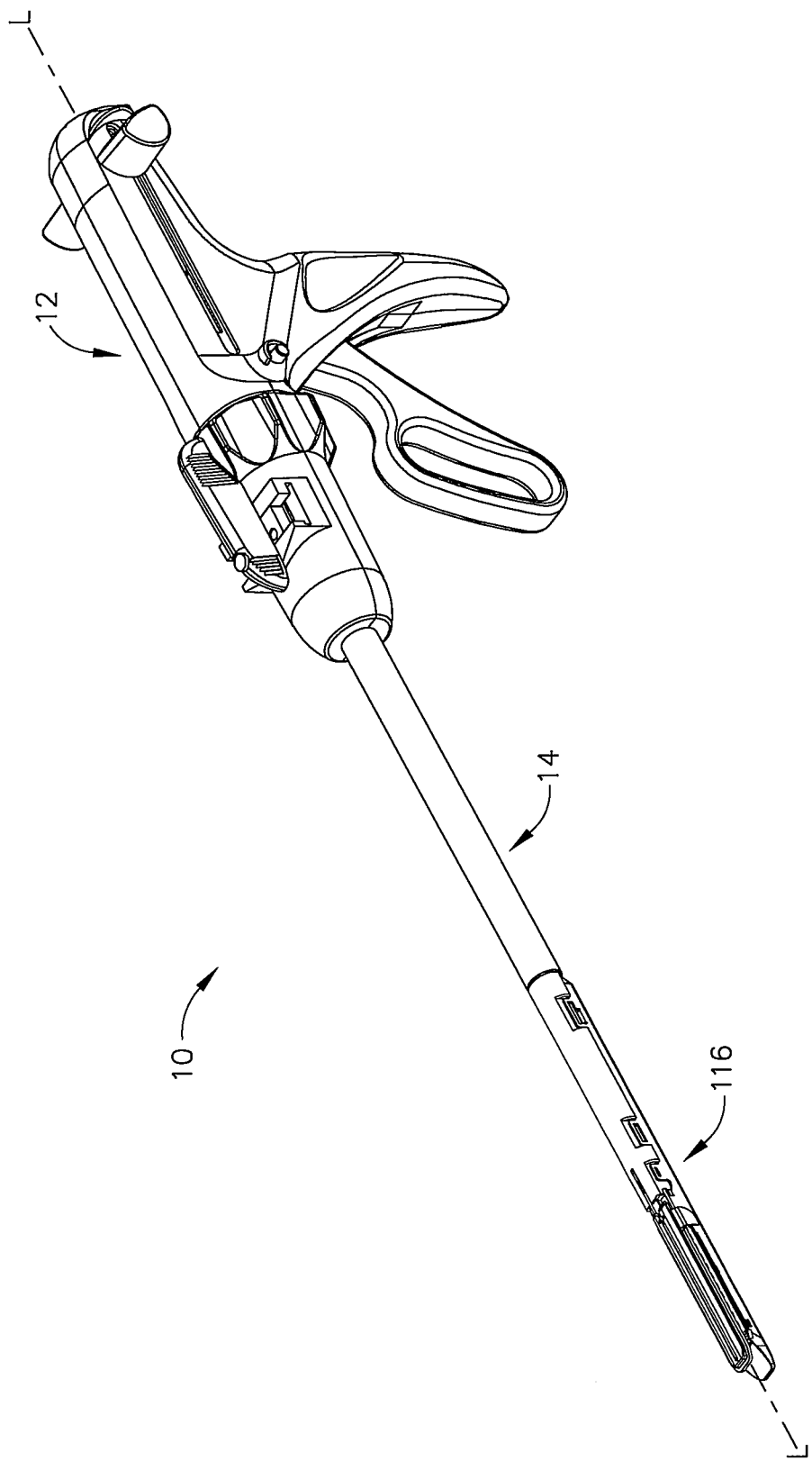
FIG. 4 is a perspective view of a non-articulatable loading unit embodiment of the present invention coupled to a surgical stapling apparatus.
Figure 5:
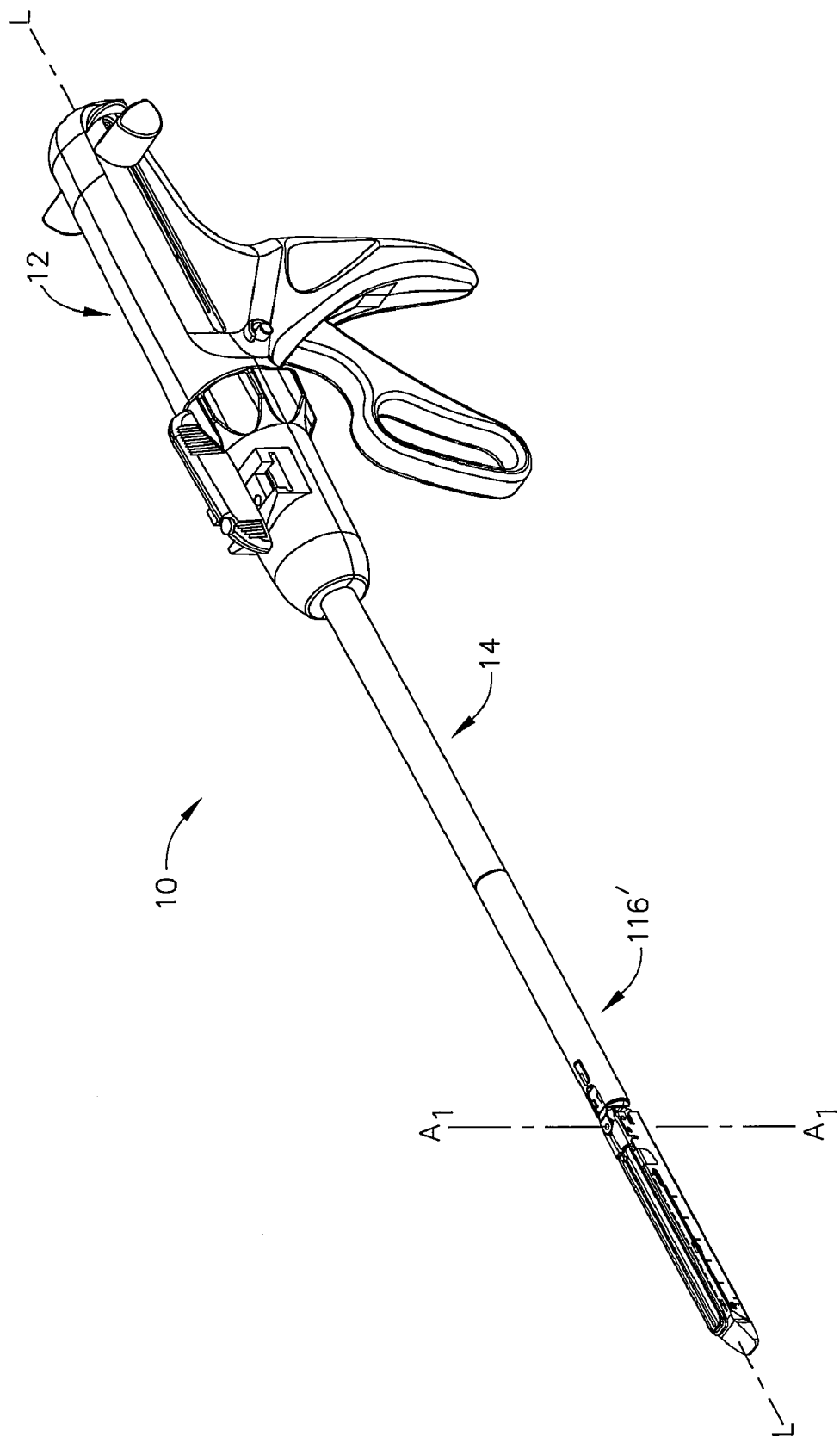
FIG. 5 is a perspective view of an articulatable disposable loading unit embodiment of the present invention coupled to a surgical stapling apparatus.

FIG. 4 illustrates a disposable loading unit 116 of the present invention employed in connection with a surgical stapling apparatus 10. FIG. 5 illustrates an articulatable disposable loading unit 116' of the present invention employed in connection with a surgical stapling apparatus 10. The non-articulatable disposable loading unit 116 of the present invention is similar to the non-articulatable loading unit 16 described above, except for the improvements of the present invention discussed in detail below. The articulatable disposable loading unit 116' is similar to the articulatable disposable loading unit 16' described above except for the improvements of the present invention discussed below. The surgical stapling apparatus 10 may include a handle assembly 12 and an elongated body 14 and be of the type and construction described in U.S. Pat. No. 5,865,361, which has been herein incorporated by reference.

Figure 6:
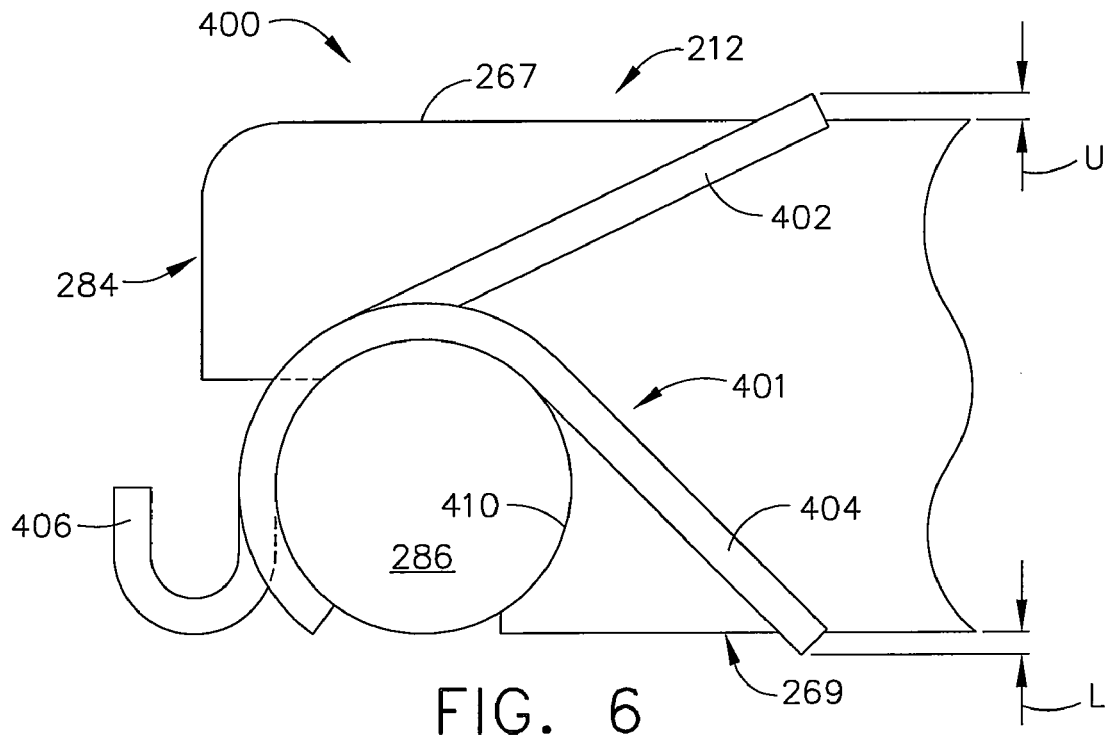
FIG. 6 is an enlarged side view of a portion of an axial drive assembly, anvil pin and pin cleat of various embodiments of the present invention.
Figure 7:
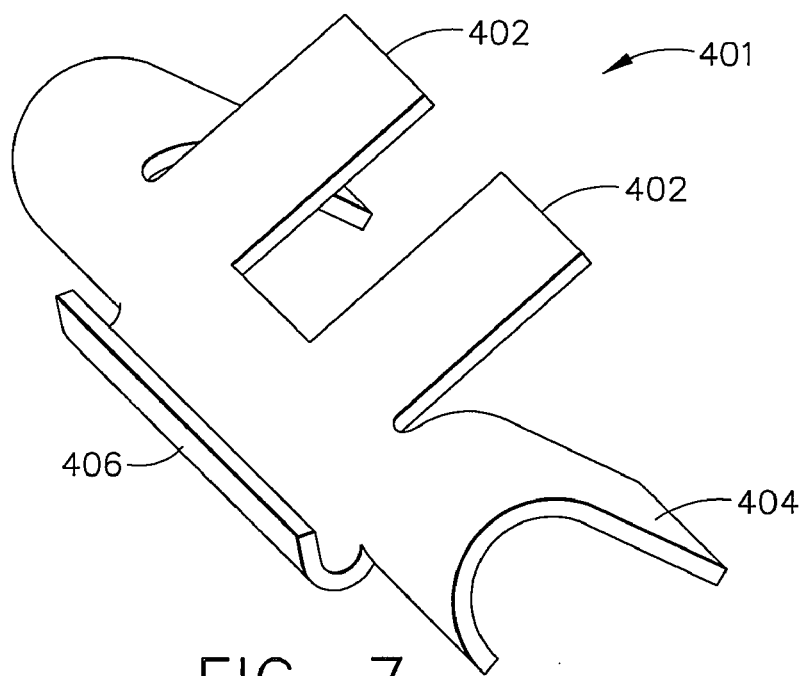
FIG. 7 is a perspective view of a pin cleat embodiment of the present invention.

FIGS. 6-12 illustrate a unique and novel anvil release assembly 400 of the present invention that may be successfully employed with the non-articulatable disposable loading unit 116 and the articulatable disposable loading unit 116' of the present invention. In these embodiments, a single camming pin 286 is employed. The camming pin 286 snaps into a socket 410 formed in the retention flange 284 of axial drive assembly 212. See FIG. 6. The anvil release assembly 400 may further include a disengagement member in the form of a pin cleat 401 of the type depicted in FIG. 7. As can be seen in that Figure, a pin cleat 401 may include at least one upper cleat portion 402 and at least one lower cleat portion 404. A stiffener 406 may be provided on the distal end of the pin cleat 400. The pin cleat 401 may be configured to snap onto or otherwise be attached to the camming pin 286. As can be seen in FIG. 6, when the pin cleat 401 is attached to the camming pin 286, the upper ends of the upper cleat portions 402 extend beyond an upper surface 267 of the retention flange portion 284 of the axial drive assembly 212 a short distance "U" and the lower cleat portions 404 extend beyond a lower surface 269 of the retention flange portion 284 of the axial drive assembly 212 a short distance "L". In various embodiments, for example, "U" and "L" may each be approximately 0.02 to 0.04 inches.

Figure 8:
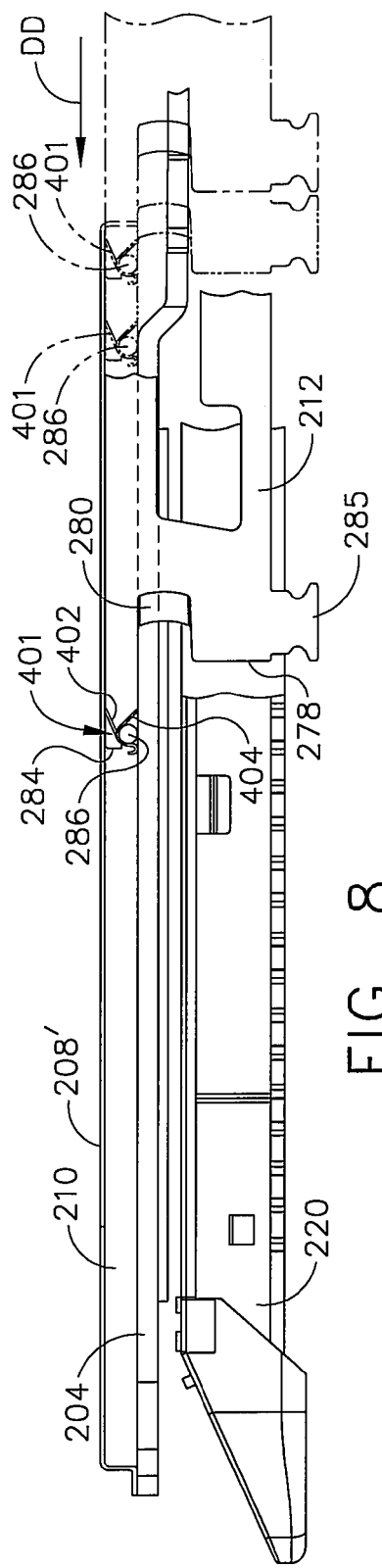
FIG. 8 is a partial cross-sectional elevational view of a disposable loading unit embodiment of the present invention wherein various positions of the axial drive assembly are illustrated in phantom lines.
Figure 9:
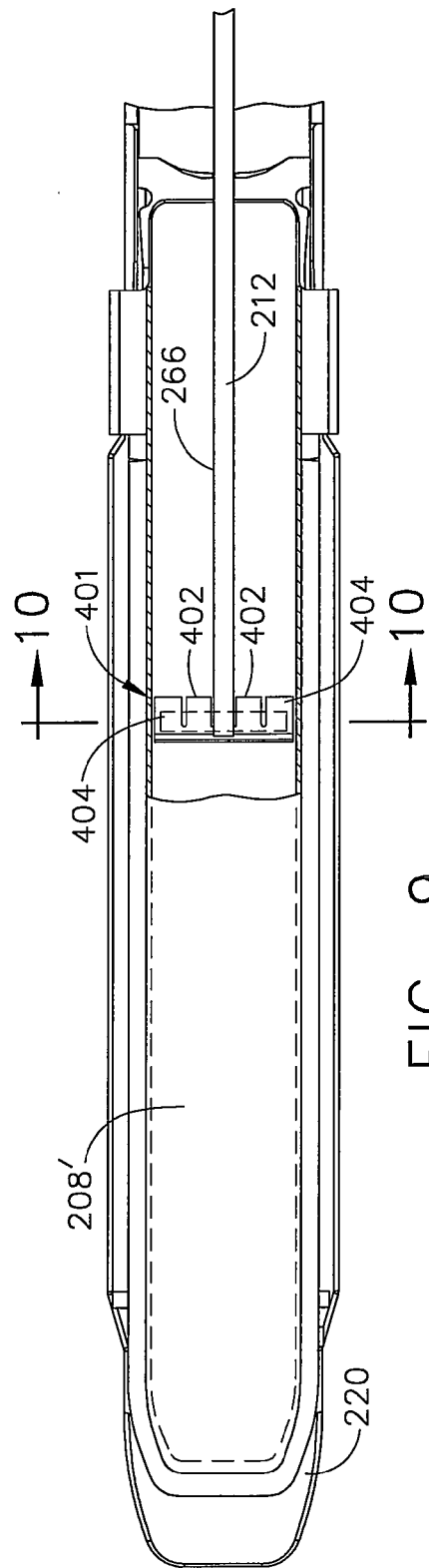
FIG. 9 is a plan view of a portion of the disposable loading unit embodiment of FIG. 8 with a portion of the anvil cover removed for clarity.

The operation of the disposable loading units 116 and 116' will be explained with reference to FIGS. 8 and 11. FIG. 8 illustrates various positions of the drive assembly 212 and the camming pin 286 and pin cleat 401 as it is driven distally through the tool assembly 17. No tissue is shown in FIG. 8. FIG. 11 illustrates tissue "T" clamped between the anvil portion 204 and the staple cartridge 220. In that Figure, however, too much tissue "T" has been clamped in the tool assembly 17 thereby causing the drive assembly 212 to become jammed as it is driven through the tissue "T" in the distal direction "DD". At that point, the clinician simply retracts the drive assembly 212 in the proximal direction "PD". As the axial drive assembly 212 is retracted, the upper and lower cleat portions 402, 404, respectively dig into the anvil cover 208' and the anvil base 204, respectively. As the retraction force continues to be applied to the axial drive assembly 212, the camming pin 286 is dislodged from the socket 410 formed in the retention flange 284 of axial drive assembly 212 thereby permitting the axial drive assembly 212 to continue in the proximal direction "PD" and also permitting the anvil assembly 20 to pivot open (arrow "P") to release the tissue "T" from the tool assembly 17. See FIG. 11. Those of ordinary skill in the art will appreciate that the camming pin 286 and the socket 410 must be sized relative to each other such that the pin 286 will become dislodged from the socket 410 as the drive assembly 212 is retracted during a jamb. Likewise, the upper cleat portions 402 and lower cleat portions 404 must be configured to dig into or otherwise engage the cover 208' and the anvil base 204, respectively as described above. It will be understood that when the anvil pin 286 is detached from the axial drive assembly 212, the pin 286 with the pin cleat 401 attached thereto remains trapped within the anvil cavity 210 formed between the anvil cover 208 and the anvil portion 204 to prevent the pin 286 from become lost in the patient.

Figure 12:
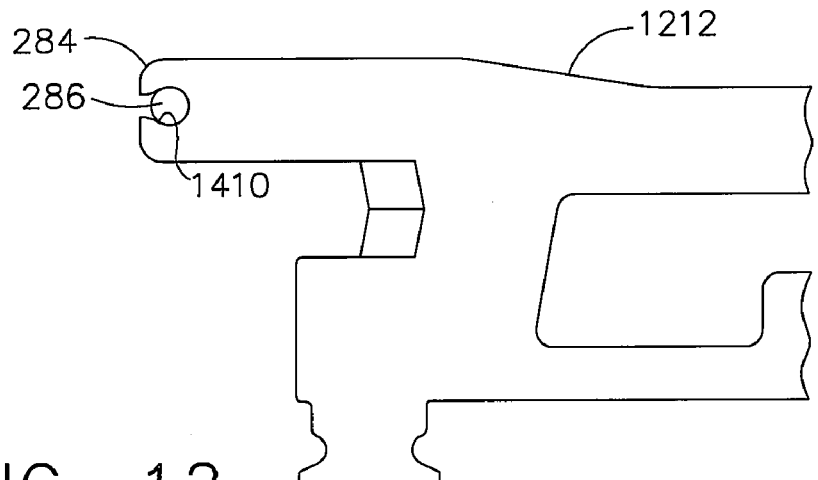
FIG. 12 is a partial side view of a portion of an axial drive assembly embodiment of the present invention.
Figure 13:
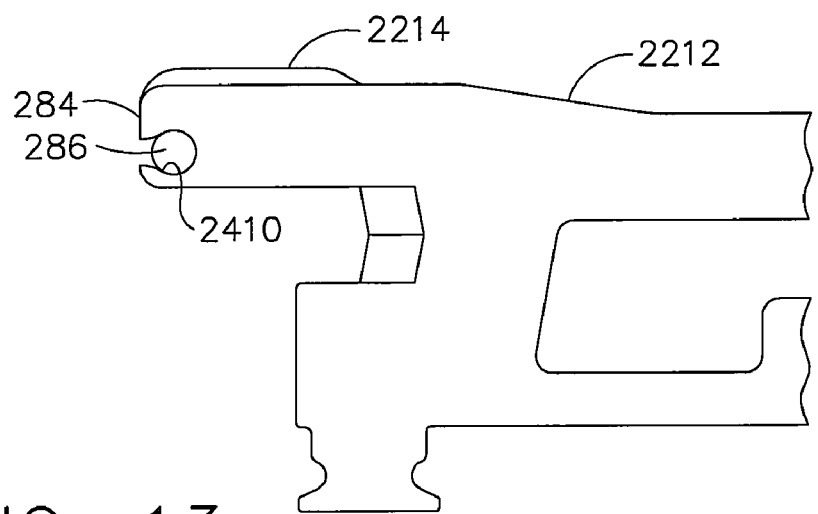
FIG. 13 is a partial side view of a portion of another axial drive assembly embodiment of the present invention.
Figure 14:
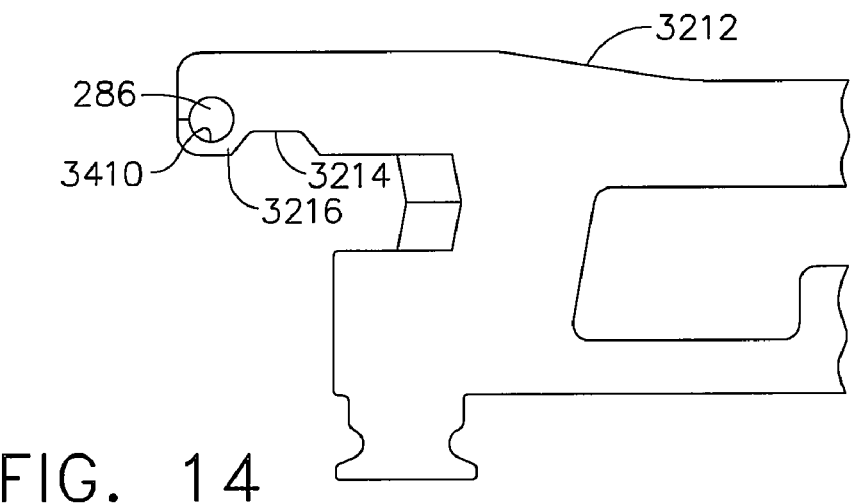
FIG. 14 is a partial side view of a portion of another axial drive assembly embodiment of the present invention.
Figure 15:
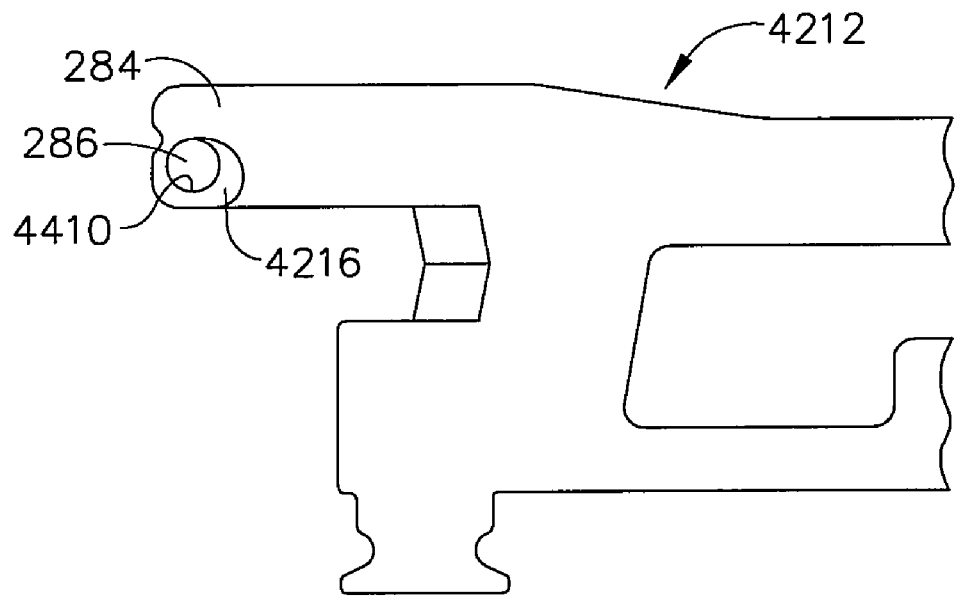
FIG. 15 is a partial side view of a portion of another axial drive assembly embodiment of the present invention.
Figure 16:
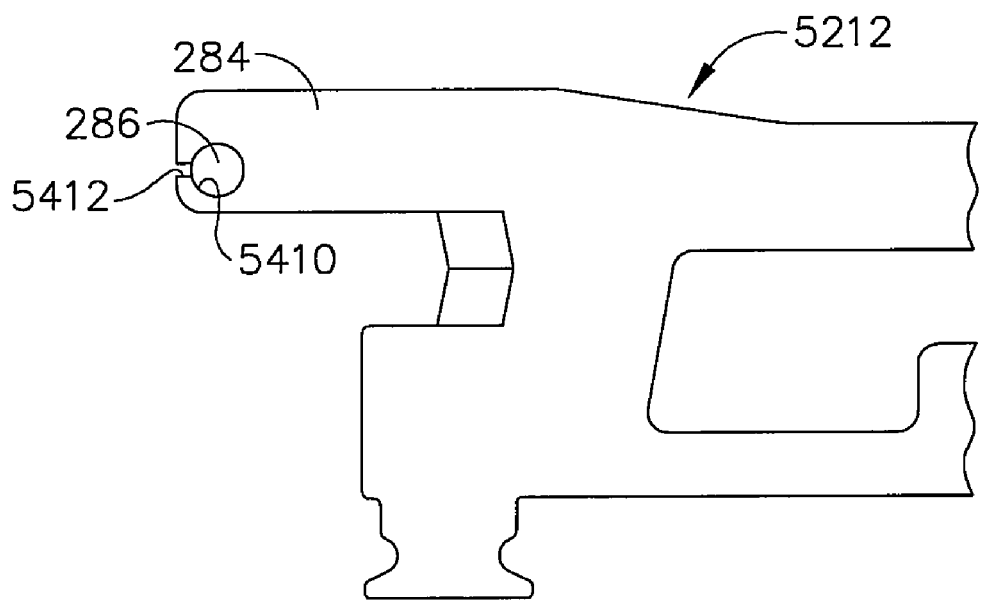
FIG. 16 is a partial side view of a portion of another axial drive assembly embodiment of the present invention.
Figure 17:
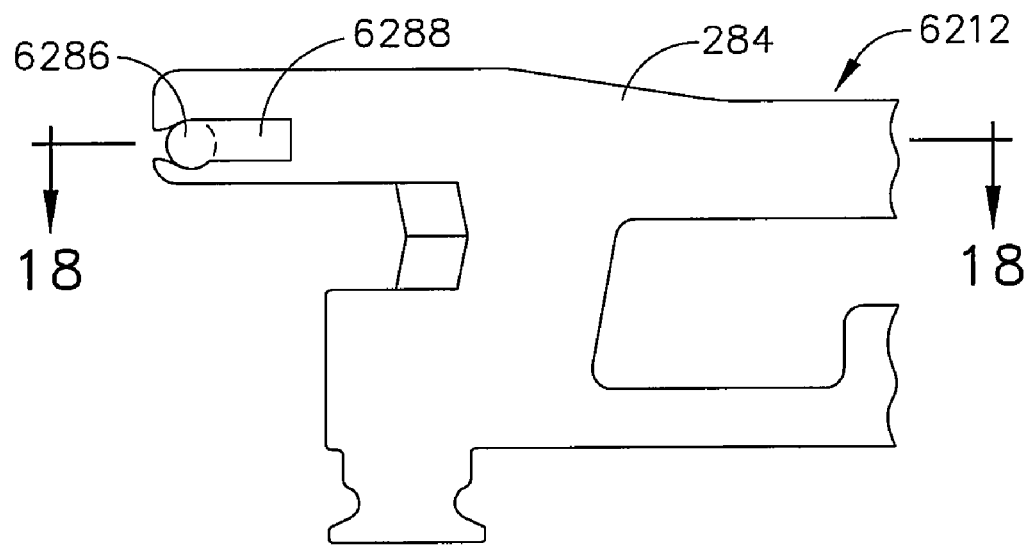
FIG. 17 is a partial side view of a portion of another axial drive assembly embodiment of the present invention.
Figure 18:
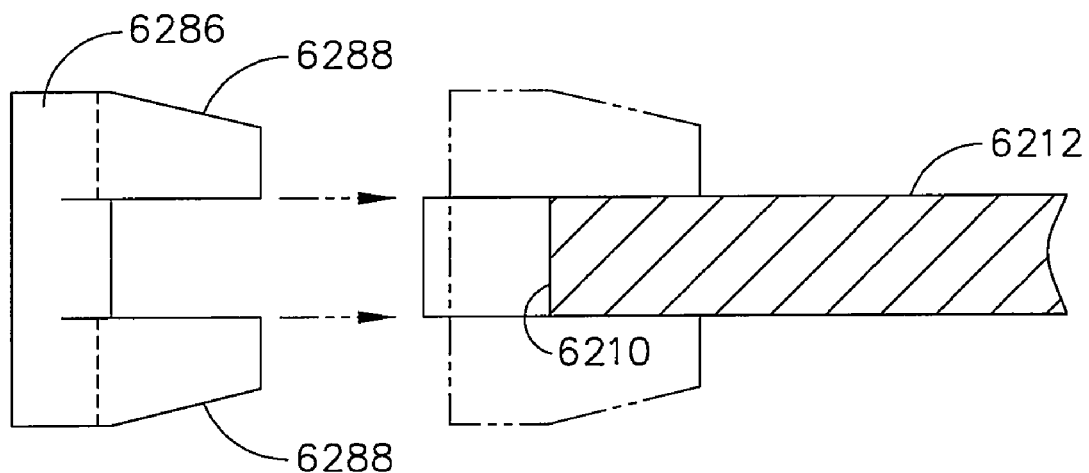
FIG. 18 is a cross-sectional view of the axial drive assembly of FIG. 17 taken along line 18-18 in FIG. 17 with the anvil pin shown prior to attachment to the axial drive assembly.

Alternative drive assembly and socket configurations are depicted in FIGS. 12-18. Similar configurations are disclosed in the commonly owned U.S. patent application Ser. No. 11/820,077, filed Jun. 18, 2007, entitled Surgical Stapling and Cutting Instrument With Improved Anvil Opening Features, to Richard W. Timm, Frederick E. Shelton, IV and Jeffrey S. Swayze, the disclosure of which is herein incorporated by reference. For example, the axial drive assembly 1212 of FIG. 12 is substantially identical to the embodiment of FIGS. 6-11, except that the slot 1410 extends into the distal end of the retention flange 284. The axial drive assembly 2212 of FIG. 13 is also similar to the embodiments of FIGS. 6-11, except that the retention flange 284 of axial drive assembly 2212 has a reinforcement member 2214 formed thereon. In the embodiment of FIG. 14, the retraction flange 284 of the axial drive assembly 3212 has an undercut portion 3214 and the slot 3410 is initially crimped closed. When the axial drive assembly 3212 is retracted, the pin cleat 400 digs in as described above, the bottom portion 3216 forming the slot 3410 is permitted to bend downward to release the pin 286. In the embodiment depicted in FIG. 15, the retention flange 284 of the axial drive assembly 4212 has a slot 4410 that is defined by a bendable flap 4216 that can be bent or deformed to open the slot 4410 to permit the pin 286 to be removed therefrom. The retention flange 284 of the axial drive assembly 5212 depicted in FIG. 16 has a second slot 5412 that communicates with the first pin slot 5410 that enables the first pin slot 5410 to be opened to a point wherein the pin 286 can be released therefrom. In the embodiment depicted in FIGS. 6-16, the pin 286 has a substantially circular cross-sectional shape. In the embodiment depicted in FIGS. 17 and 18, the pin 6286 has a portion with a cross-sectional shape sized to be received in slot 6210 and also has lateral wings or gussets 6288 for providing additional support to the pin 6286 and minimize any likelihood of the pin 6286 bending as the axial drive assembly 6212 is driven in the distal direction "DD".

Figure 19:
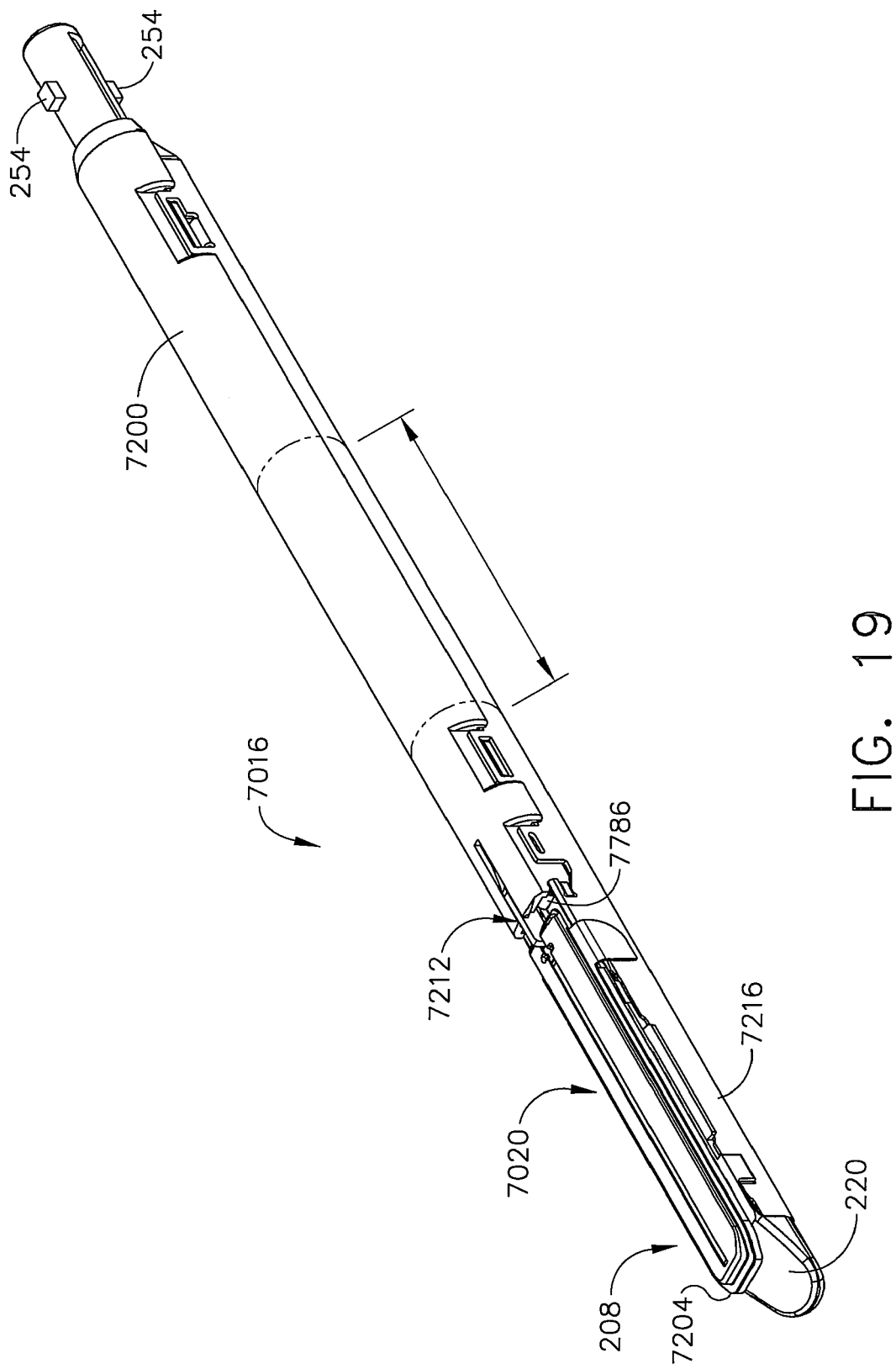
FIG. 19 is a perspective view of another disposable loading unit embodiment of the present invention.
Figure 20:
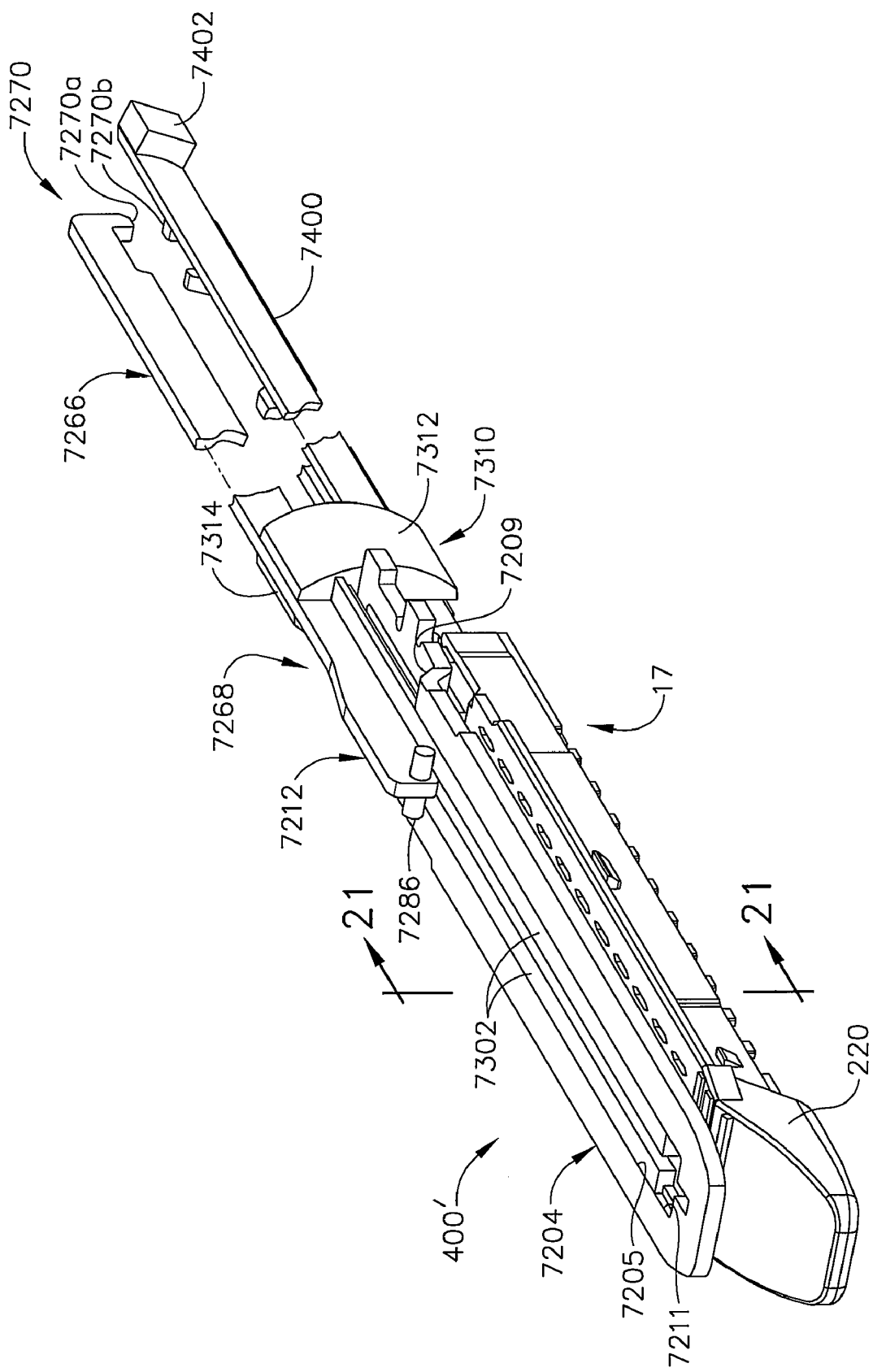
FIG. 20 is a perspective view of a portion of the disposable loading unit of FIG. 19 with some components thereof removed for clarity.

FIGS. 19-22 illustrate another disposable loading unit 7016 of the present invention that may be substantially similar to the non-articulatable disposable loading unit 16 described above, except for the unique and novel improvements described below. As can be seen in FIGS. 19 and 20, the disposable loading unit 7016 includes a tool assembly 17 that includes a staple cartridge 220 that houses a plurality of surgical staples therein. The tool assembly 17 also includes a staple-forming anvil assembly 7020. Such disposable loading unit 7016 may perform surgical procedures such as cutting tissue and applying staples on each side of the cut. Anvil assembly 7020 generally includes and anvil portion 7204 that has a plurality of staple deforming concavities (not shown) formed in the undersurface thereof. A cover plate 208 is commonly secured to a top surface of anvil portion 7204 to define an anvil cavity 210 therebetween. The anvil cavity 210 is dimensioned to receive a distal end of an axial drive assembly 7212. A camming surface 7209 is formed on a proximal end of anvil portion 7204 and is positioned for engagement by a camming pin 7286 that is attached to a retention flange 7284 of the axial drive assembly 7212 to facilitate closing of the anvil assembly 7020.

The disposable loading unit 7016 also includes a carrier 7216 that supports the staple cartridge 220 in a manner described above. A housing portion 7200 may be adapted to snap onto or otherwise be attached to the carrier 7216. The axial drive assembly 7212 may include an elongated drive beam 7266 that has a distal working head 7268 and a proximal engagement section 7270. The drive beam 7266 may be constructed from a single sheet of material or, preferably, from multiple stacked sheets. Engagement section 7270 includes a pair of engagement fingers 7270a and 7270b that are dimensioned and configured to mountingly engage a drive member as was discussed above. As noted above, the drive member may include a proximal porthole configured to receive the distal end of a control rod.

Figure 21:
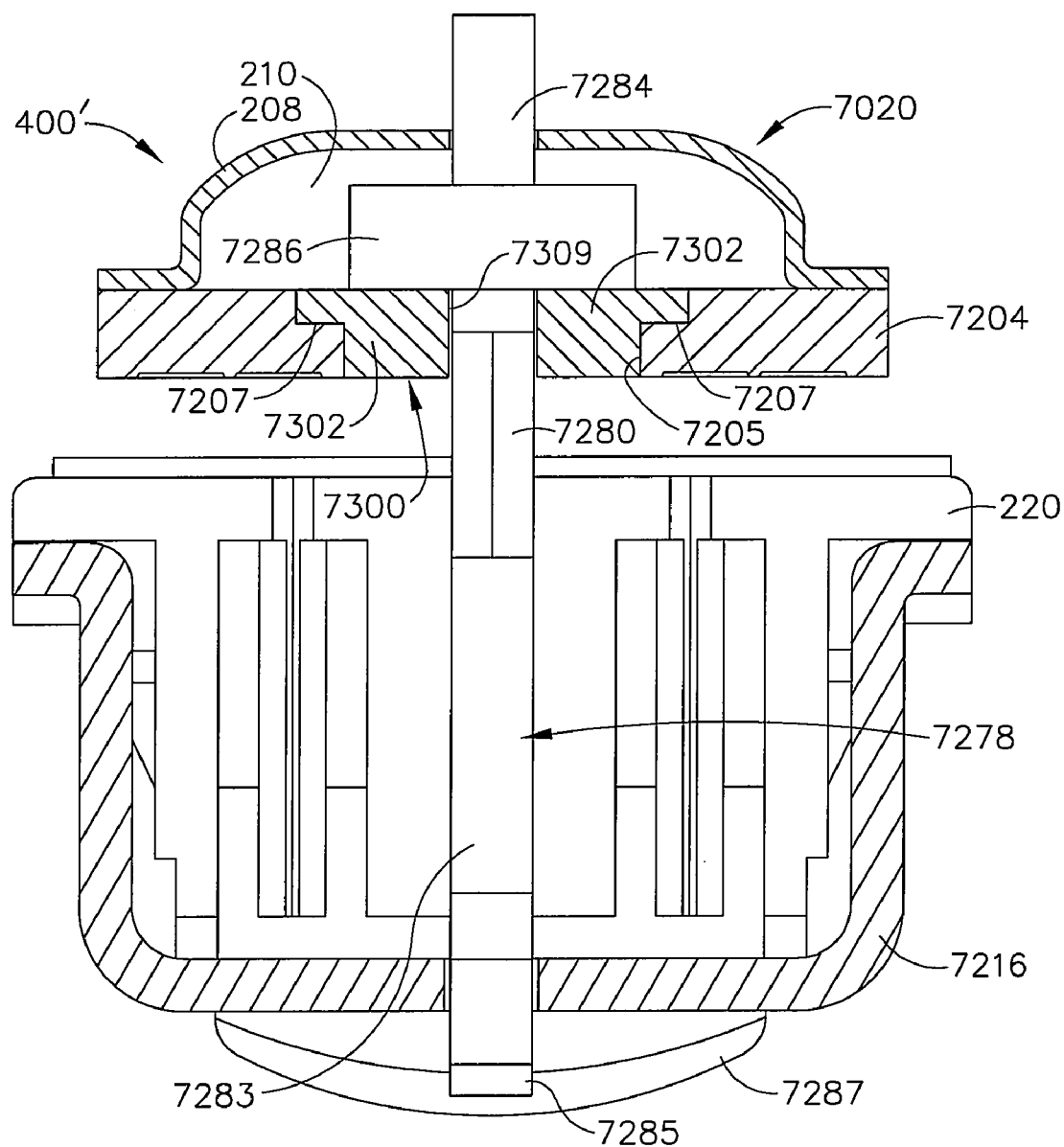
FIG. 21 is a cross-sectional view of the disposable loading unit depicted in FIG. 20 taken along line 21-21 in FIG. 20.
Figure 22:
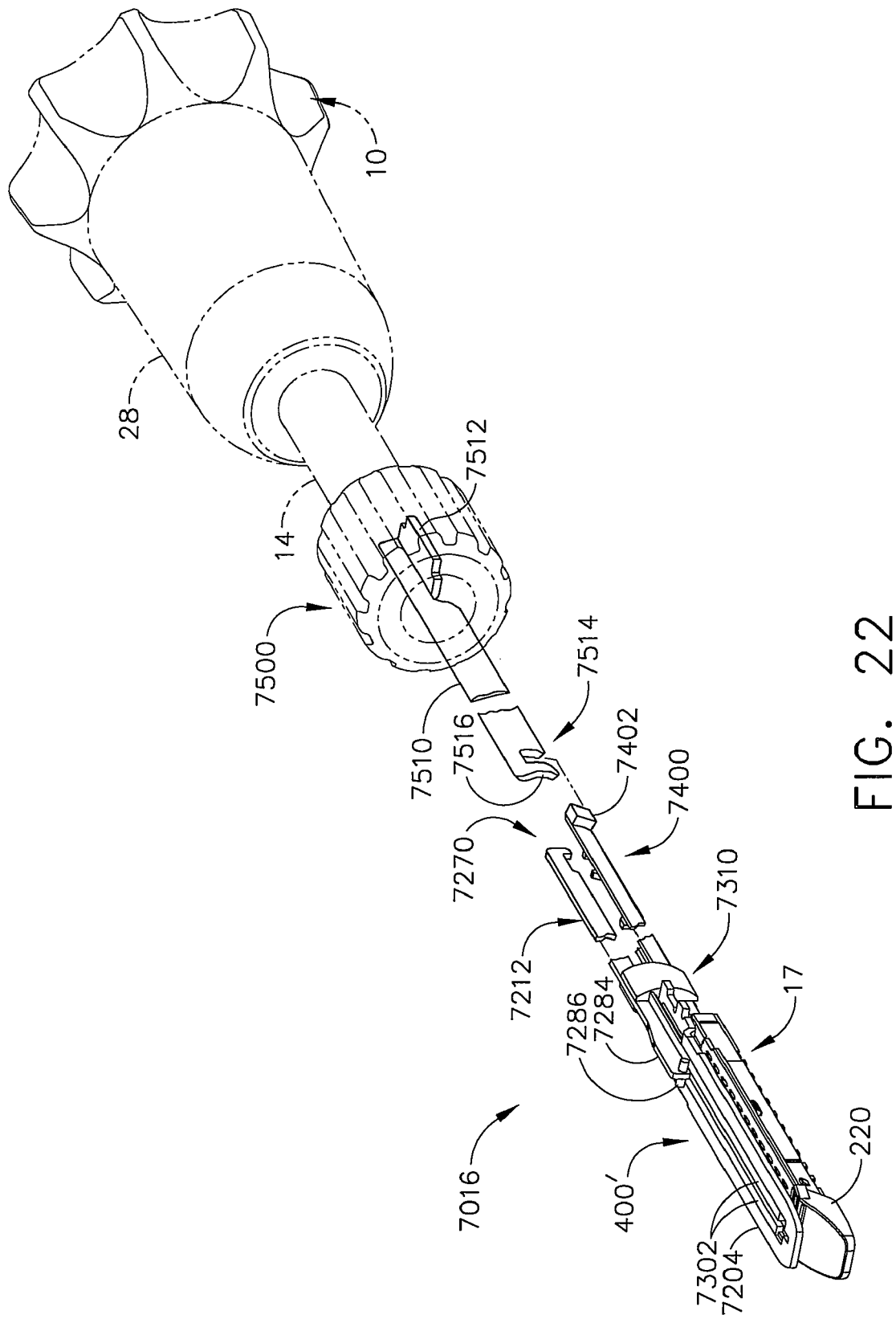
FIG. 22 is a partial perspective view of the disposable loading unit of FIGS. 19-21 with portions of a surgical stapling apparatus to which it is attached shown in phantom lines.

As shown in FIG. 21, the distal end of drive beam 7266 includes a vertical support strut 7278 which supports the knife blade 7280, and an abutment surface 7283 which engages the central portion of an actuation sled during a stapling procedure. Surface 7285 at the base of surface 7283 is configured to receive a support member 7287 that is slidably positioned along the bottom of the carrier 7216. Knife blade 7280 is generally positioned to translate slightly behind actuation sled through a central longitudinal slot in staple cartridge 220 to form an incision between rows of stapled body tissue.

A retention flange 7284 projects distally from vertical strut 7278 and supports a camming pin 7286 at its distal end. Camming pin 7286 is dimensioned and configured to engage camming surface 7209 on anvil portion 7204 to clamp anvil portion 7204 against body tissue. In addition, a leaf spring may be provided between the proximal end of the anvil portion 7204 and the distal end portion of the housing 7200 to bias the anvil assembly 7020 to a normally open position.

The embodiments depicted in FIGS. 19-22 employ a an anvil release assembly 400' that includes a unique and novel retractable anvil support assembly 7300 that may comprise a pair of anvil support bars 7302 that are received in an opening 7305 in the anvil portion 7204 and are supported on corresponding ledges 7207 formed therein. See FIG. 21. The anvil support bars 7302 are supported in spaced-apart relation to each other to define an elongate slot 7309 therebetween to receive the vertical support strut 7278 and the knife blade 7280 therethrough. As can be seen in that Figure, when the anvil support bars 7302 are supported on their respective ledges 7207, the camming pin 7286 rides thereon to force the anvil assembly 7020 into the tissue-clamping position towards the staple cartridge 220. The proximal end 7304 of each anvil support bar 7302 may be attached to a slide base 7310 that is configured to axially slide within the carrier 7216 and the housing 7200. Slide base 7310 may comprise a left portion 7312 and right portion 7314 that are located on opposing sides of the drive assembly 7212. Attached to the slide base 7310 is a release connector link 7400 that may have a detent 7402 on its proximal end.

The disposable loading unit 7016 may be used in connection with a conventional surgical stapling apparatus 10 of the type disclosed in U.S. Pat. No. 5,865,361 that has been modified in the following manner. In particular, the surgical stapling apparatus 10 has a rotatable knob 28 that has an elongated body 14 attached thereto. The elongated body 14 is configured to operably interface with the detents 254 in the proximal end of the disposable loading unit 7016 in a known manner. However, an actuator knob 7500 is slidably received on the elongated body 14 of the surgical stapling apparatus 10 and is attached to an actuator bar 7510 that is received within the elongated body 14 and has a proximal end 7512 that extends through an axial slot (not shown) in the elongated body 14. The actuator bar 7510 also has a distal end 7514 that has a hook 7516 that is adapted to releasably engage the detent 7402 on the connector link 7400 when the disposable loading unit 7016 is coupled to the distal end of the elongate body 14. See FIG. 22.

During use, the retractable support bars 7302 are positioned as illustrated in FIGS. 20 and 21. When in that position, the support bars 7302 support the camming pin 7286 thereon such that the camming pin retains the anvil assembly 7020 in the tissue-clamping position. As can be seen in FIG. 20, the support bars 7302 are received in the opening in the anvil portion 7204 and serve to define a pin-receiving opening in the anvil portion 7204 for the camming pin to extend therethrough when the axial drive assembly 7212 has reached the end of the firing stroke (e.g., its distal-most position) to enable the anvil assembly 7020 to pivot to the open position to release the tissue therefrom. If, however, during the firing stroke, the axial drive assembly 7212 becomes jammed, the clinician can release the tissue from the tool assembly 17 simply by grasping the actuator knob 7500 and moving it axially on the elongate body 14 in the proximal direction "PD". As the actuator knob 7500 is moved in the proximal direction "PD", the support bars 7302 are also retracted to a point wherein the support bars 7302 no longer support the camming pin 7286 an thus permits the camming pin 7286 to pass through the axially extending slot 7205 in the anvil portion 7204. As the camming pin 7286 passes through the slot 7205, the anvil assembly 7020 is permitted to move to the open position wherein the tool assembly may be released from the tissue. As can be seen in FIG. 19, the disposable loading unit 7016 is longer than a convention disposable loading unit 16 by a distance "D" which is the distance required to provide a desired amount of clearance for retracting the support bars 7302 into the housing assembly 7200. Thus, the clinician can release the anvil assembly 7020 (e.g., declamp the tissue) should the axial drive assembly 7212 become jammed at any point during the firing stroke.

Figure 23:
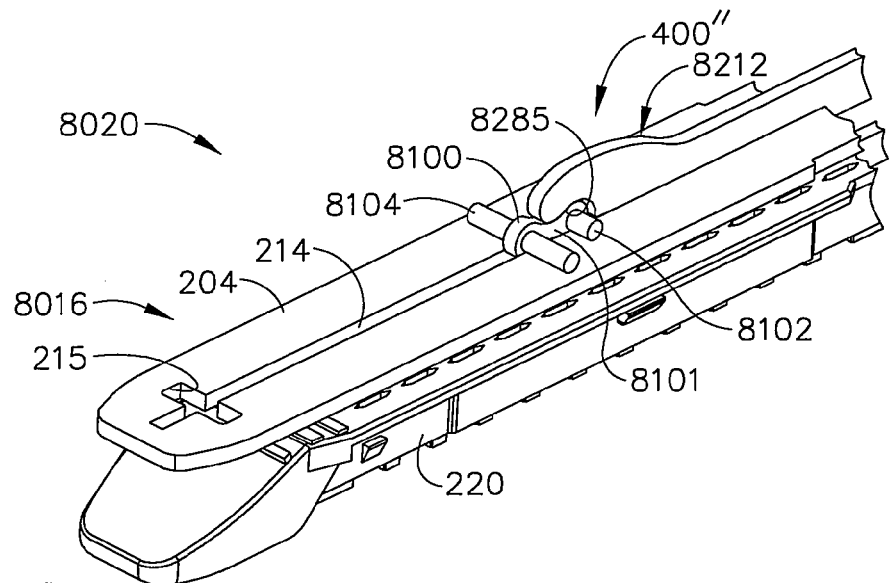
FIG. 23 is a perspective view of a portion of a disposable loading unit embodiment of the present invention wherein the axial drive assembly is partially through its firing stroke.
Figure 24:
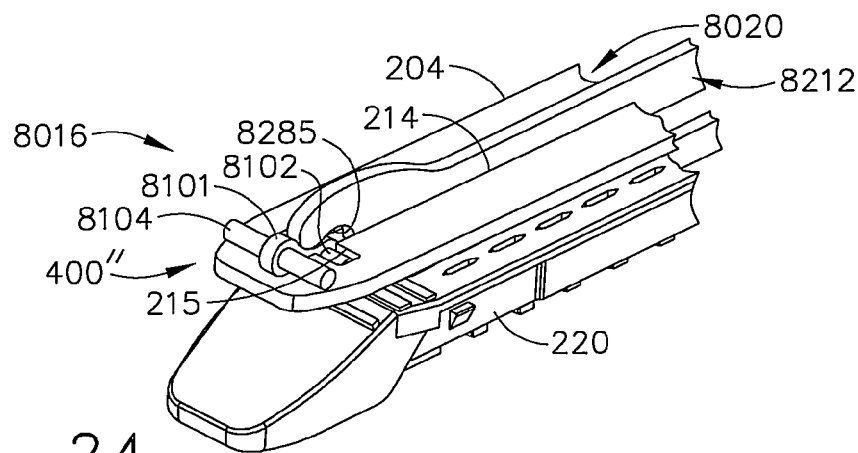
FIG. 24 is another perspective view of the portion of the disposable loading unit depicted in FIG. 23 with the axial drive assembly at the end of its firing stroke.
Figure 25:
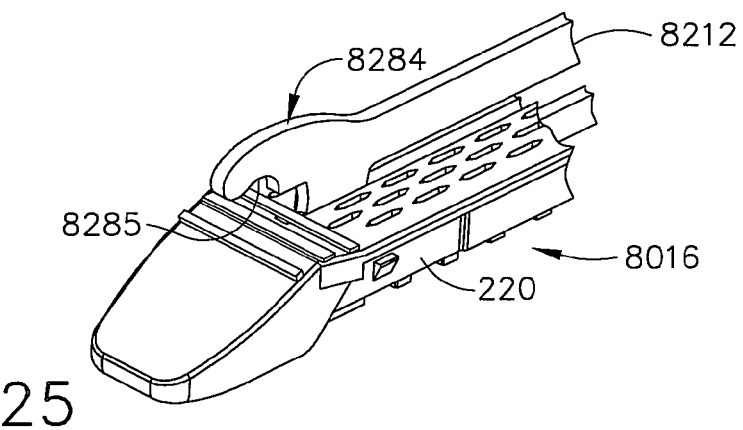
FIG. 25 is another perspective view of the portion of eth disposable loading unit depicted in FIGS. 23 and 24 after the retainer assembly has been disengaged from the axial drive assembly.
Figure 26:
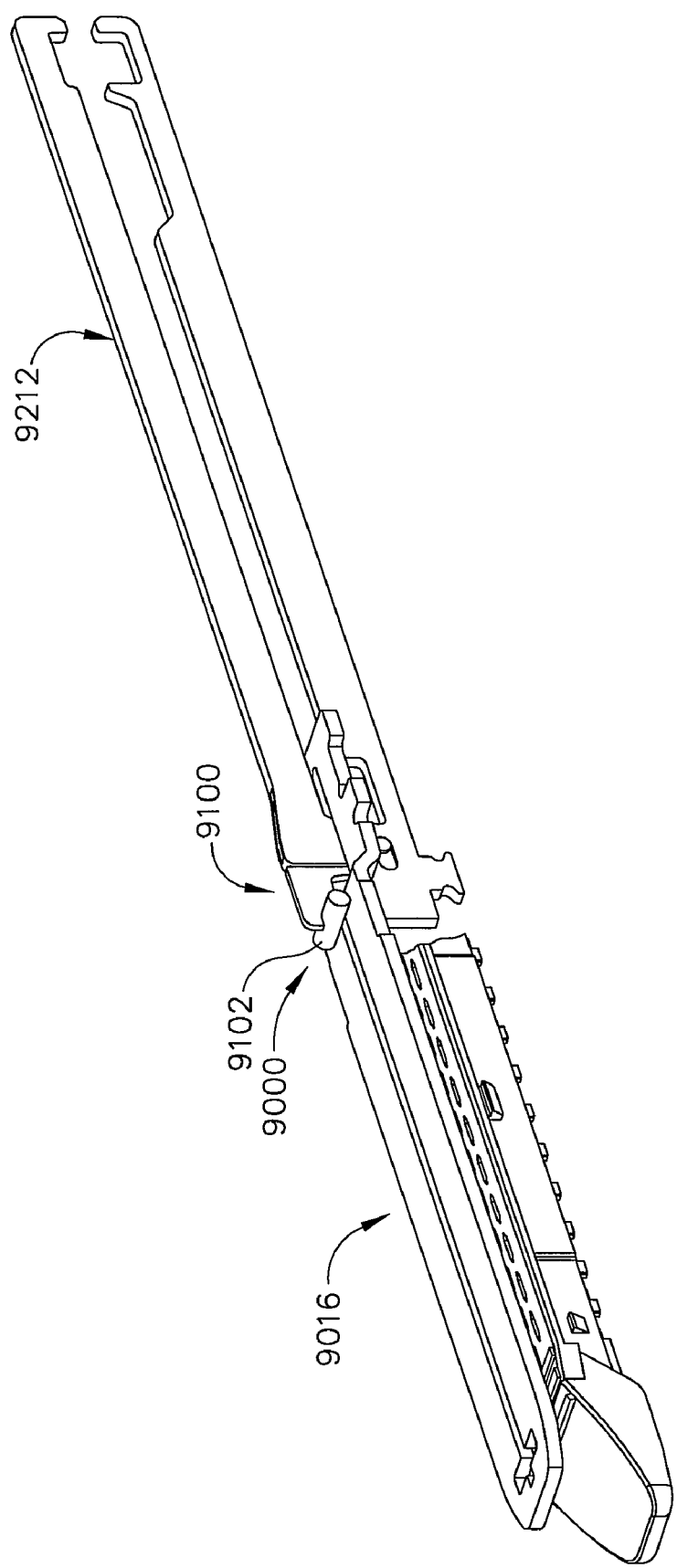
FIG. 26 is a partial perspective view of a portion of another disposable loading unit of the present invention with some components thereof removed for clarity.

FIGS. 23-25 illustrate a portion of an alternative disposable loading unit 8016 that may be substantially identical to the disposable loading units 16, 16' except for the unique and novel improvements discussed below. For example, this embodiment employs an anvil release assembly 400" that comprises a movable retainer assembly 8100. In various embodiments, the retainer assembly 8100 may comprise a retainer body 8101 that has an anvil pin 8102 and a retainer pin 8104 mounted thereon. The retainer assembly 8100 is sized to slide within the axial slot 214 in the anvil portion 204 and is configured to releasably engage a corresponding notch 8285 in the retainer portion 8284 of the axial drive assembly 8212. The axial drive assembly 8212 may otherwise be similar to the axial drive assembly 212 as was described above. The retainer assembly 8100 and the notch 8285 are configured such that the retainer assembly are loosely coupled as the axial drive assembly 8212 is driven through the staple cartridge, yet when the axial drive assembly 8212 is retracted, the frictional forces between the retainer assembly 8100 and the anvil portion 204 retain the retainer assembly 8100 in position and thereby enable axial drive assembly 8212 to decouple therefrom. When the axial drive assembly 8212 decouples from the retainer assembly 8100, the anvil assembly 8020 is permitted to pivot to the open position. Thus, should the axial drive assembly 8212 become jammed at any point during the firing stroke, the clinician can simply retract the axial drive assembly 8212 which causes it to decouple from the retainer assembly 8100 and thereby permits the anvil assembly 8020 to pivot open and release the tissue therein. As can be seen in FIGS. 24 and 25, when the axial drive assembly 8212 has reached the end of the firing stroke, the anvil pin 8102 falls into the transverse slot 215 in the anvil portion 204 and thereby facilitate the decoupling of the axial drive assembly 8212 from the retainer assembly 8100 to enable the anvil assembly 8020 to pivot to the open position. See FIG. 25. It will be appreciated that when the anvil assembly 82020 pivots to the open position, the retainer assembly 8100 remains with the anvil portion 204 because the retainer pin 8104 is larger than the transverse slot 215. Thus, the retainer assembly 8100 will not become decoupled from the anvil assembly 8020 and possibly become lost in the patient.

Figure 27:
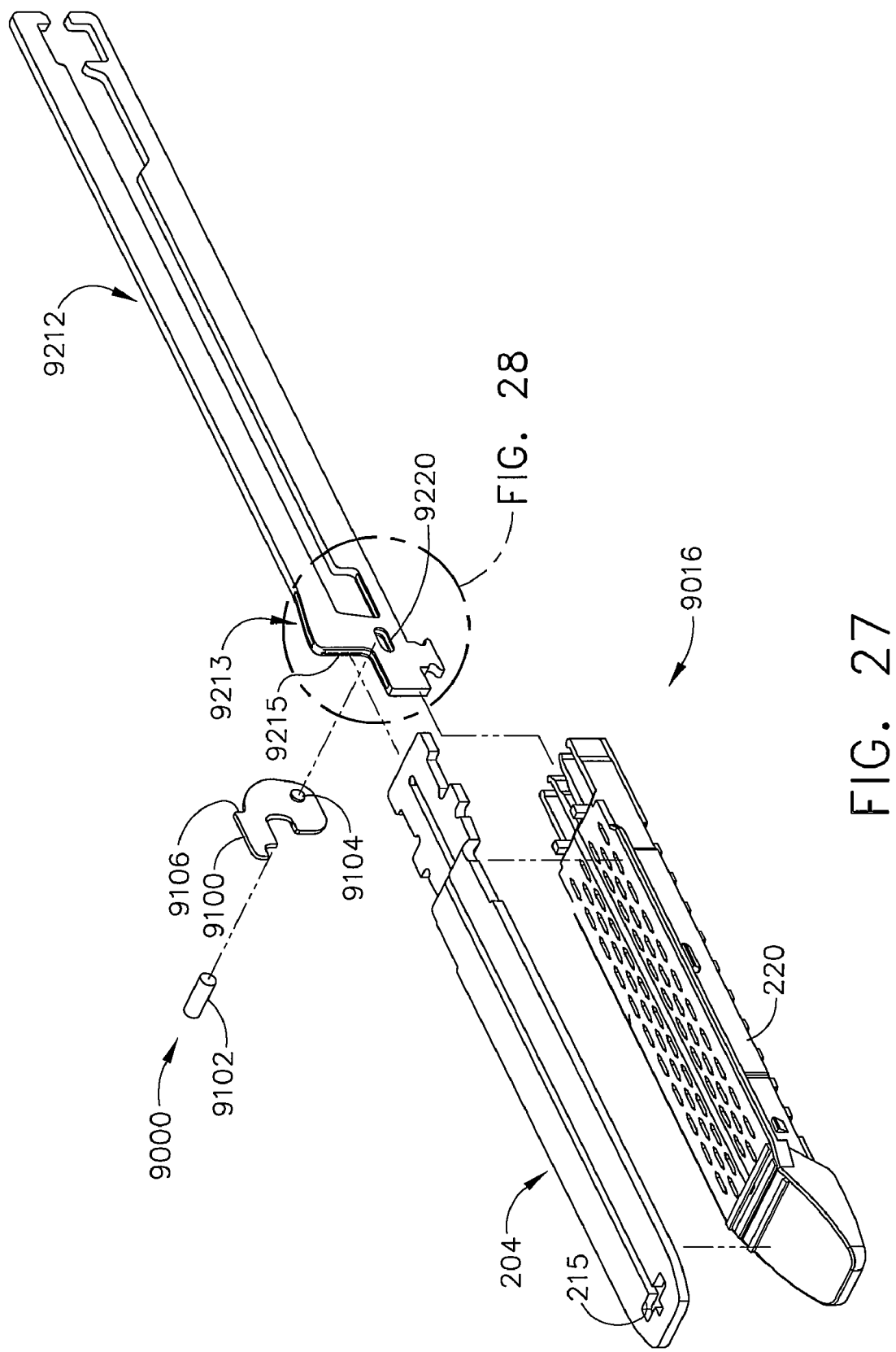
FIG. 27 is an exploded assembly view of the portion of disposable loading unit depicted in FIG. 26.
Figure 28:
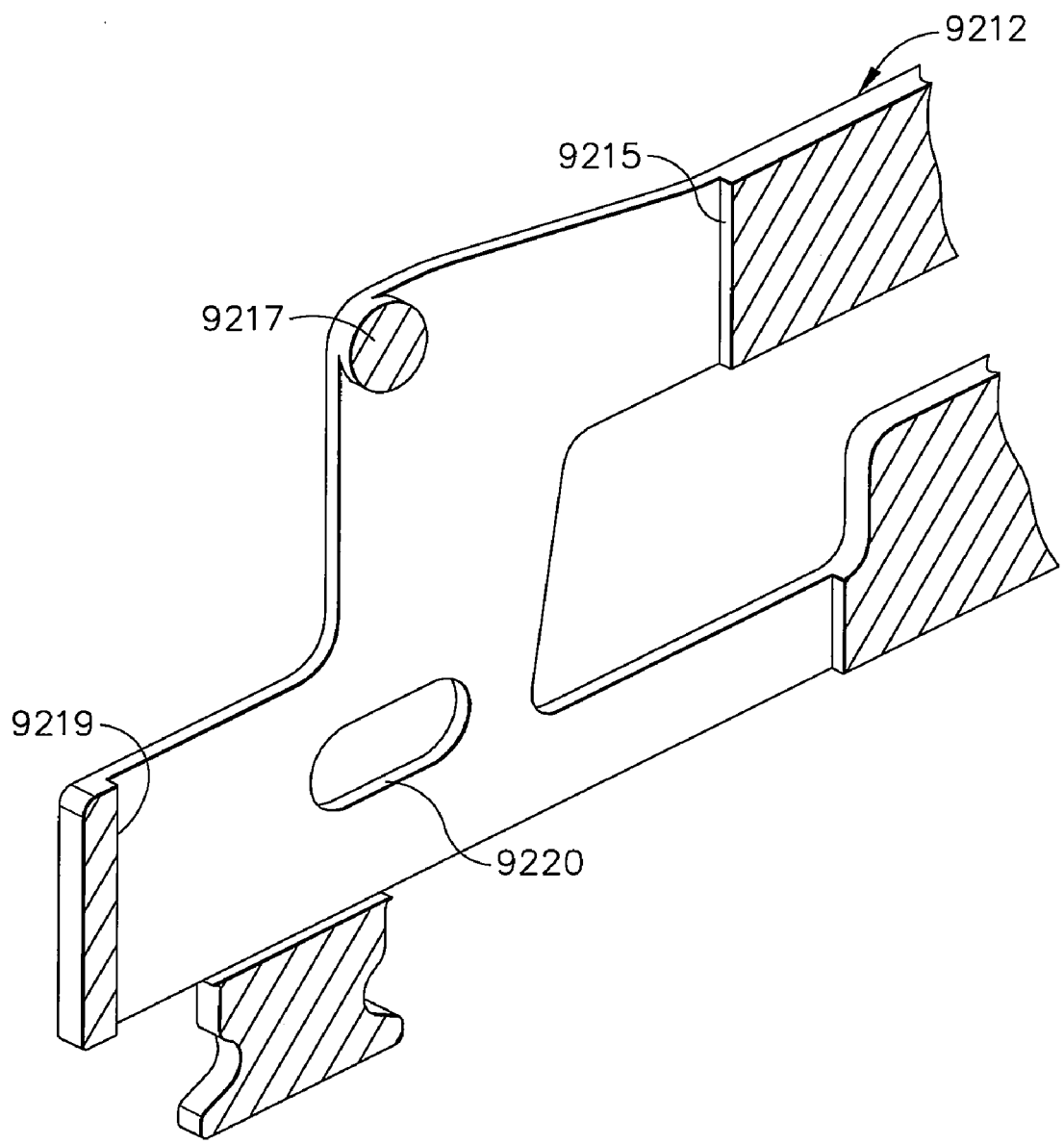
FIG. 28 is a cross-sectional view of a portion of the axial drive assembly depicted in FIG. 27.
Figure 29:
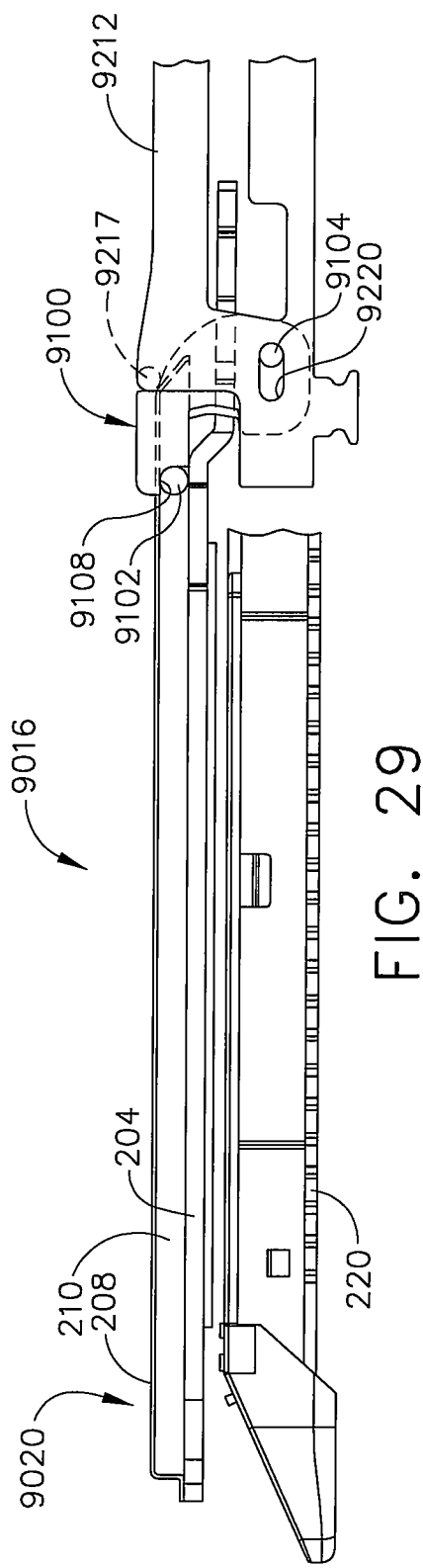
FIG. 29 is a side elevational view of the disposable loading unit of FIGS. 26-28 with some components thereof removed for clarity.

FIGS. 26-32 illustrate a portion of an alternative disposable loading unit 9016 that may be substantially identical to the disposable loading units 16, 16' except for the unique and novel improvements discussed below. For example, this embodiment employs an anvil release assembly 9000 that includes a pivotable anvil arm 9100 that is adapted to releasably engage an anvil pin 9102. The pivotable anvil arm 9100 is sized to be received within a slot 9215 formed in a bifurcated distal end 9213 of an axial drive assembly 9212. The axial drive assembly 9212 may otherwise be similar to the axial drive assembly 212 as was described above. More specifically and with reference to FIG. 28, the distal end 9213 may be formed with a thrust stop 9217, a distal ledge 9219 and a pivot slot 9220. As can be seen in FIG. 27, the pivotable anvil arm 9100 has a trunion 9104 that protrudes from each lateral side thereof to be received in the pivot slot 9220. The top of the pivotable anvil arm 9100 has a thrust notch 9106 formed therein for engagement with the thrust stop 9217 on the axial drive assembly 9212. The upper distal end of the pivotable anvil arm 9100 also has a pin notch 9108 formed therein for engagement with the anvil pin 9102. The anvil pin 9102 may be provided with a groove (not shown) therein adapted to frictionally receive a portion of the pivotable anvil arm 9100 to releasably couple the anvil pin 9102 of the pivotable anvil arm 9100. Other methods may be employed to releasably couple the anvil pin 9102 to the pivotable anvil arm 9100 without departing from the spirit and scope of the present invention.

Figure 30:
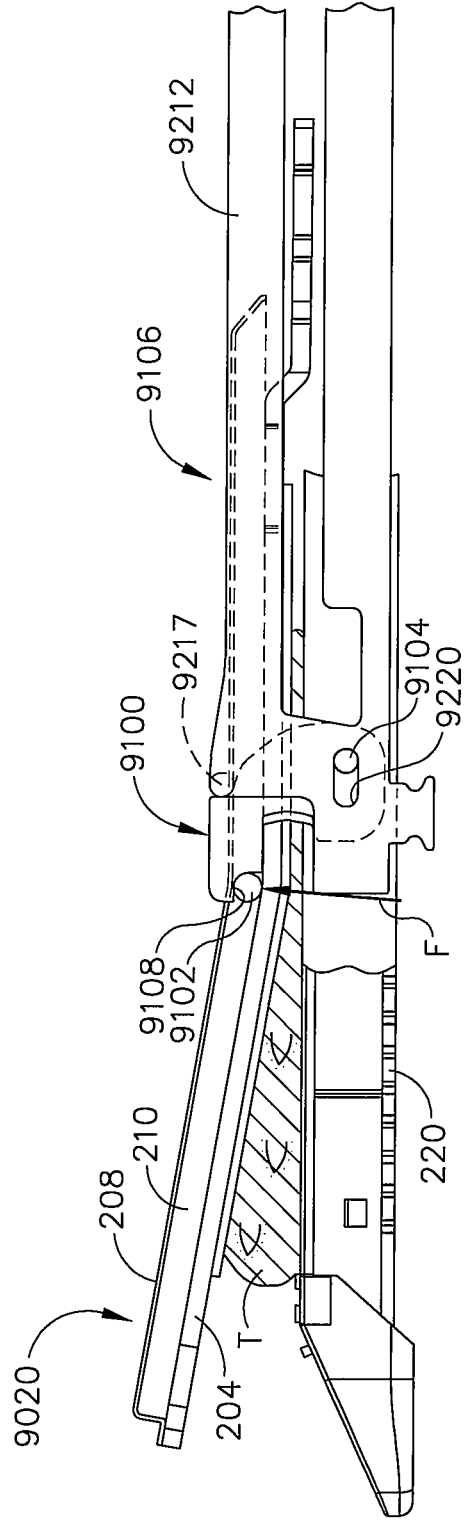
FIG. 30 is a side view of the disposable loading unit of FIG. 29 wherein tissue has been clamped between the anvil assembly thereof and the staple cartridge.

Operation of the disposable loading unit 9016 will now be described with reference to FIGS. 30-32. FIG. 30 illustrates a portion of tissue "T" clamped in the disposable loading unit 9016 wherein the axial drive assembly 9212 has become jammed. As can be seen in that Figure, the pivot pin 9104 is located in the proximal end of the slot 9220 and the force "F" that is generated by the tissue located between the anvil portion 204 and the staple cartridge 220 is pushing upward on the anvil pin 9102. To release the tissue "T", the clinician retracts the axial drive assembly 9212 in the proximal direction "PD" which enables the anvil arm 9100 to pivot as illustrated by arrow "P" in FIG. 31. As the anvil assembly 9020 pivots upward, the force "F" on the anvil pin 9102 dissipates. Movement of the axial drive assembly 9212 in the proximal direction a distance that is substantially equal to the length of the slot 9220 enables the pivot pin to be completely released from the anvil arm 9100 as illustrated in FIG. 32 to thereby enable the anvil assembly 9020 to pivot to the open position. When this happens, the anvil pin 9102 is retained within the anvil cavity 210 formed between the anvil portion 204 and the anvil cover plate 208.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A disposable loading unit for attachment to a surgical stapling apparatus, said disposable loading unit comprising:
   a staple cartridge supported in a carrier operably couplable to the surgical stapling apparatus;
   an anvil assembly movably coupled to said carrier for selective movable travel between open and closed positions relative to said staple cartridge;
   an axial drive assembly having a distal end portion constructed to move in a distal direction through a slot in said staple cartridge in response to a drive motion imparted to said axial drive assembly from the surgical stapling apparatus and also move in a proximal direction through said slot in said staple cartridge in response to a retraction motion applied to said axial drive assembly from the surgical stapling apparatus, said distal end portion of said axial drive assembly configured to impart a closing force to said anvil assembly as said axial drive assembly is driven in said distal direction in said slot in said staple cartridge; and
   an anvil release assembly operably cooperating with said distal end portion of said axial drive assembly and said anvil assembly for selectively causing said distal end portion of said axial drive assembly to discontinue imparting said closing force to said anvil assembly regardless of where said distal end portion of said axial drive assembly is located within said slot in said staple cartridge,
   wherein said anvil release assembly comprises:
      an anvil pin releasably coupled to said distal end portion of said axial drive assembly and positioned to impart said closing force to said anvil assembly as said distal end portion of said axial drive assembly is driven in said distal direction; and
      a disengagement member interfacing with said anvil pin to decouple said anvil pin from said distal end portion of said axial drive assembly upon application of the retraction motion to said axial drive assembly.

2. The disposable loading unit of claim 1 wherein said retraction member comprises a pin cleat attached to said anvil pin and configured to engage at least a portion of said anvil assembly as the retraction motion is applied to said axial drive assembly and thereby cause said anvil pin to be decoupled therefrom.

3. A disposable loading unit for attachment to a surgical stapling apparatus, said disposable loading unit comprising:
   a staple cartridge supported in a carrier operably couplable to the surgical stapling apparatus;
   an anvil assembly movably coupled to said carrier for selective movable travel between open and closed positions relative to said staple cartridge;
   an axial drive assembly having a distal end portion constructed to move in a distal direction through a slot in said staple cartridge in response to a drive motion imparted to said axial drive assembly from the surgical stapling apparatus and also move in a proximal direction through said slot in said staple cartridge in response to a retraction motion applied to said axial drive assembly from the surgical stapling apparatus, said distal end portion of said axial drive assembly configured to impart a closing force to said anvil assembly as said axial drive assembly is driven in said distal direction in said slot in said staple cartridge; and
   an anvil release assembly operably cooperating with said distal end portion of said axial drive assembly and said anvil assembly for selectively causing said distal end portion of said axial drive assembly to discontinue imparting said closing force to said anvil assembly regardless of where said distal end portion of said axial drive assembly is located within said slot in said staple cartridge,
   wherein said anvil release assembly comprises a support assembly movably supported by said anvil assembly and being selectively movable between a first position wherein said distal end portion of said axial drive assembly imparts said closing force thereto and retracted positions wherein said distal end portion of said axial drive assembly cannot impart said closing force thereto to thereby enable said anvil assembly to move to said open position.

4. The disposable loading unit of claim 3 wherein said support assembly comprises a pair of support bars movably supported within an axial slot in said anvil assembly, said support bars spaced from each other to permit said distal end portion of said axial drive assembly to movably pass therebetween, said support bars selectively movable between said first position wherein said support bars support an anvil pin on said distal end portion of said axial drive assembly and said retracted positions wherein said anvil pin is not supported by said support bars and is permitted to disengage the anvil assembly.

5. The disposable loading unit of claim 4 wherein said support assembly further comprises:
   a retraction link coupled to said support bars; and
   an actuator knob operably supported on a portion of the surgical stapling apparatus and configured to be removably coupled to the retraction link to enable retraction motions to be applied thereto upon actuation of said actuator knob.

6. A disposable loading unit for attachment to a surgical stapling apparatus, said disposable loading unit comprising:
   a staple cartridge supported in a carrier operably couplable to the surgical stapling apparatus;
   an anvil assembly movably coupled to said carrier for selective movable travel between open and closed positions relative to said staple cartridge;
   an axial drive assembly having a distal end portion constructed to move in a distal direction through a slot in said staple cartridge in response to a drive motion imparted to said axial drive assembly from the surgical stapling apparatus and also move in a proximal direction through said slot in said staple cartridge in response to a retraction motion applied to said axial drive assembly from the surgical stapling apparatus, said distal end portion of said axial drive assembly configured to impart a closing force to said anvil assembly as said axial drive assembly is driven in said distal direction in said slot in said staple cartridge; and
   an anvil release assembly operably cooperating with said distal end portion of said axial drive assembly and said anvil assembly for selectively causing said distal end portion of said axial drive assembly to discontinue imparting said closing force to said anvil assembly regardless of where said distal end portion of said axial drive assembly is located within said slot in said staple cartridge, wherein said anvil release assembly comprises a retainer movably supported by said anvil assembly and releasably coupled to said distal end portion of said axial drive assembly such that upon application of the retraction motion to said axial drive assembly, said retainer is decoupled therefrom to thereby enable the anvil assembly to move to the open position.

7. The disposable loading unit of claim 6 wherein said retainer comprises:
   a retainer body sized to axially move within an axially extending first anvil slot in said anvil assembly and configured to releasably engage a retainer notch in said distal end of said axial drive assembly;
   a transverse anvil pin coupled to said retainer body such that said anvil pin spans said axially extending first anvil slot in said anvil assembly and is sized to pass through a second anvil slot located at a distal end of said first anvil slot; and
   a transverse retainer pin coupled to said retainer body such that said retainer pin spans said first anvil slot and is unable to pass through said second anvil slot.

8. A disposable loading unit for attachment to a surgical stapling apparatus, said disposable loading unit comprising:
   a staple cartridge supported in a carrier operably couplable to the surgical stapling apparatus;
   an anvil assembly movably coupled to said carrier for selective movable travel between open and closed positions relative to said staple cartridge;
   an axial drive assembly having a distal end portion constructed to move in a distal direction through a slot in said staple cartridge in response to a drive motion imparted to said axial drive assembly from the surgical stapling apparatus and also move in a proximal direction through said slot in said staple cartridge in response to a retraction motion applied to said axial drive assembly from the surgical stapling apparatus, said distal end portion of said axial drive assembly configured to impart a closing force to said anvil assembly as said axial drive assembly is driven in said distal direction in said slot in said staple cartridge; and
   an anvil release assembly operably cooperating with said distal end portion of said axial drive assembly and said anvil assembly for selectively causing said distal end portion of said axial drive assembly to discontinue imparting said closing force to said anvil assembly regardless of where said distal end portion of said axial drive assembly is located within said slot in said staple cartridge,
   wherein said anvil release assembly comprises:
      an anvil arm movably coupled to said distal end portion of said axial drive assembly; and
      a transverse anvil pin detachably engaged with said an anvil arm and positioned to impart said closing force to said anvil assembly as said distal end of said axial drive assembly is driven in said distal direction and become detached from said anvil arm upon application of a retraction force to said axial drive assembly.

9. The disposable loading unit of claim 8 wherein said anvil arm is movably coupled to said axial drive assembly such that said anvil arm can move axially relative to said axial drive assembly and pivot relative to said axial drive assembly.

10. A disposable loading unit for attachment to a surgical stapling apparatus, said disposable loading unit comprising:
    a staple cartridge supported in a carrier operably couplable to the surgical stapling apparatus;
    an anvil portion pivotally coupled to said carrier for selective pivotable travel between open and closed positions relative to said staple cartridge, said anvil portion having an axial anvil slot therethrough;
    an anvil cover attached to said anvil portion to define an anvil cavity therebetween;
    an axial drive assembly having a distal end portion constructed to move in a distal direction through a cartridge slot in said staple cartridge and said anvil slot in response to a drive motion imparted to said axial drive assembly from the surgical stapling apparatus and also move in a proximal direction through said cartridge slot and said anvil slot in response to a retraction motion applied to said axial drive assembly from the surgical stapling apparatus;
    a transverse anvil pin detachably supported on a retention flange portion of said axial drive assembly such that said anvil pin is movably received in said anvil cavity and spans said anvil slot; and
    a disengagement member on said transverse anvil pin oriented to engage at least a portion of at least one of said anvil cover and said anvil portion when a retraction motion is applied to said axial drive assembly regardless of where said distal end portion of said axial drive assembly is located within said cartridge slot to thereby cause said anvil pin to be decoupled from said axial drive assembly.

11. The disposable loading unit of claim 10 wherein said disengagement member comprises a pin cleat attachable to said anvil pin and having at least one upper cleat portion oriented to retainingly engage a portion of said anvil cover and at least one lower cleat portion oriented to retainingly engage a portion of said anvil portion.

12. The disposable loading unit of claim 10 wherein said anvil pin is retained within said anvil cavity when said anvil pin has been detached from said axial drive assembly.

13. The disposable loading unit of claim 10 wherein said anvil pin is supported in an open ended slot in said retention flange portion of said axial drive assembly.

14. The disposable loading unit of claim 10 wherein said anvil pin is supported in a slot in said retention flange portion of said axial drive assembly and wherein said retention flange portion has an undercut portion formed therein adjacent said slot to permit a bottom portion of said retention flange portion forming a portion of said slot to move away from an upper portion of said slot to permit said anvil pin to be removed from said slot by interaction of said disengagement member with at least one of said anvil cover and said anvil portion upon application of the retraction motion to said axial drive assembly.

15. The disposable loading unit of claim 10 wherein said anvil pin is supported in a slot in said retention flange portion of said axial drive assembly and wherein said slot is formed by a bendable flap formed in said retention flange portion such that upon interaction of said disengagement member with at least one of said anvil cover and said anvil portion, said anvil pin causes said bendable flap to move to a position wherein said anvil pin may be detached from said retention flange portion.

16. The disposable loading unit of claim 10 wherein said anvil pin has at least one reinforcement flap formed thereon.

17. A surgical stapling apparatus, comprising:
    a handle assembly;
    an elongated body operably coupled to said handle assembly;

a disposable loading unit operably coupled to said elongated body, said disposable loading unit comprising:
  a carrier operably couplable to a distal end of said elongated body;
  a staple cartridge supported in said carrier;
  an anvil assembly movably coupled to said carrier for selective movable travel between open and closed positions relative to said staple cartridge;
  an axial drive assembly having a distal end portion constructed to move in a distal direction through a slot in said staple cartridge in response to a drive motion imparted to said axial drive assembly from said handle assembly and also move in a proximal direction through said slot in said staple cartridge in response to a retraction motion applied to said axial drive assembly from said handle assembly, said distal end portion of said axial drive assembly configured to impart a closing force to said anvil assembly as said axial drive assembly is driven in said distal direction in said slot in said staple cartridge;
  a pair of support bars movably supported within an axial slot in said anvil assembly, said support bars spaced from each other to permit said distal end portion of said axial drive assembly to movably pass therebetween, said support bars selectively movable between said first position wherein said support bars support an anvil pin on said distal end portion of said axial drive assembly and retracted positions wherein said anvil pin is not supported by said support bars and is permitted to disengage the anvil assembly; and
  a connector link coupled to said to said support bars; and
  a retraction link operably supported in said elongated body and configured to operably engage said connector link; and
  an actuator knob operably supported on said elongated body and interacting with said retraction link to enable retraction motions to be applied to said retraction link and said connector link upon actuation of said actuator knob.

18. The surgical stapling apparatus of claim 17 further comprising:
  a housing portion operably couplable to said distal end of said elongated body; and
  an articulation joint operably coupled to said carrier and said housing portion.

19. An axial drive assembly for a surgical instrument having an anvil assembly movable between an open and closed positions relative to a staple cartridge supported therein, said axial drive assembly comprising:
  an anvil pin releasably coupled to a distal end portion of said axial drive assembly and positioned to impart a closing force to said anvil assembly as said distal end portion of said axial drive assembly is driven in a distal direction; and
  a disengagement member interfacing with said anvil pin to decouple said anvil pin from said distal end portion of said axial drive assembly upon application of a retraction motion to said axial drive assembly.

20. An anvil release assembly for a surgical instrument having an anvil that is movable between an open and closed positions in response to opening and closing forces applied thereto by a distal end of an axial, drive assembly of the surgical instrument, wherein the anvil release assembly selectively causes the axial drive assembly to discontinue imparting the closing force to the anvil assembly regardless of where the distal end portion of the axial drive assembly is located along the anvil, said anvil release assembly comprising a support assembly movably supported by said anvil assembly and being selectively movable between a first position wherein said distal end portion of said axial drive assembly imparts said closing force thereto and retracted positions wherein said distal end portion of said axial drive assembly cannot impart said closing force thereto to thereby enable said anvil assembly to move to said open position.

21. An anvil release assembly for a surgical instrument having an anvil that is movable between an open and closed positions in response to opening and closing forces applied thereto by a distal end of an axial drive assembly of the surgical instrument, wherein the anvil release assembly selectively causes the axial drive assembly to discontinue imparting the closing force to the anvil assembly regardless of where the distal end portion of the axial drive assembly is located along the anvil, said anvil release assembly comprising a retainer movably supported by said anvil assembly and releasably coupled to said distal end portion of said axial drive assembly such that upon application of the retraction motion to said axial drive assembly, said retainer is decoupled therefrom to thereby enable the anvil assembly to move to the open position.

22. An anvil release assembly for a surgical instrument having an anvil that is movable between an open and closed positions in response to opening and closing forces applied thereto by a distal end of an axial drive assembly of the surgical instrument, wherein the anvil release assembly selectively causes the axial drive assembly to discontinue imparting the closing force to the anvil assembly regardless of where the distal end portion of the axial drive assembly is located along the anvil, said anvil release assembly comprises:
  an anvil arm movably coupled to said distal end portion of said axial drive assembly; and
  a transverse anvil pin detachably engaged with said an anvil arm and positioned to impart said closing force to said anvil assembly as said distal end of said axial drive assembly is driven in said distal direction and become detached from said anvil arm upon application of a retraction force to said axial drive assembly.

23. An axial drive assembly for a surgical instrument having an anvil portion movable between an open and closed positions relative to a staple cartridge supported in the surgical instrument, wherein the anvil portion has an anvil cover and a longitudinal slot therein through which a distal end of the axial drive assembly may move, said axial drive assembly comprising:
  a transverse anvil pin detachably supported on a retention flange portion on said distal end of said axial drive assembly such that said anvil pin is movably received in an anvil cavity and spans the slot therein; and
  a disengagement member on said transverse anvil pin oriented to engage at least a portion of at least one of the anvil cover and said anvil portion when a retraction motion is applied to said axial drive assembly regardless of where the distal end portion of said axial drive assembly is located within said slot to thereby cause said anvil pin to be decoupled from said axial drive assembly.

* * * * *